(12) United States Patent
Anderson et al.

(10) Patent No.: US 9,005,982 B2
(45) Date of Patent: Apr. 14, 2015

(54) BIOMARKERS ASSOCIATED WITH AUTOIMMUNE DISEASES OF THE LUNG

(75) Inventors: Mark S. Anderson, Larkspur, CA (US); Anthony K. Shum, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/703,617

(22) PCT Filed: Jun. 10, 2011

(86) PCT No.: PCT/US2011/040060
§ 371 (c)(1),
(2), (4) Date: Feb. 13, 2013

(87) PCT Pub. No.: WO2011/156766
PCT Pub. Date: Dec. 15, 2011

(65) Prior Publication Data
US 2013/0212720 A1      Aug. 15, 2013

Related U.S. Application Data

(60) Provisional application No. 61/354,184, filed on Jun. 11, 2010.

(51) Int. Cl.
| | |
|---|---|
| *G01N 33/00* | (2006.01) |
| *G01N 33/48* | (2006.01) |
| *G01N 33/50* | (2006.01) |
| *G01N 33/68* | (2006.01) |
| *A01K 67/027* | (2006.01) |
| *G01N 33/564* | (2006.01) |

(52) U.S. Cl.
CPC .......... *G01N 33/6884* (2013.01); *A01K 67/027* (2013.01); *G01N 33/564* (2013.01); *A01K 2227/101* (2013.01); *A01K 2227/105* (2013.01); *A01K 2227/106* (2013.01); *A01K 2267/0325* (2013.01); *G01N 2800/12* (2013.01); *G01N 2800/50* (2013.01)

(58) Field of Classification Search
USPC .............................. 435/7.1; 436/63, 503, 506
See application file for complete search history.

(56) References Cited

FOREIGN PATENT DOCUMENTS

WO    WO-2008/066483        6/2008

OTHER PUBLICATIONS

Shum et al, Sci Transl. Med. 1(9):9ra20, 1-10, 2009.*
Khanna et al, J. Rheumatol. 30(6):1248-1252, 2003.*
Hunninghake et al, Am. J. Pathol. 97:149-206, 1979.*
Zhao et al, Q. J. Med. 89:259-265, 1996.*
Marra et al, J. Immunol. 148(2):532-537, 1992.*
Schultz et al, Clinica Chimica Acta 384:12-23, 2007.*
Bingle et al, Trends in Immunol. 25(2): 53-55, 2007.*
GenBank AX752831.1 (Oct. 2008), Sequence 1 from Patent EP1310558.
NCBI Reference Sequence NM_001025574.1 (Apr. 2013), *Mus musculus* BPI fold containing family B, member 9B (Bpifb9b), mRNA. First seen at NCBI on Jul. 16, 2005.
NCBI Reference Sequence NM_033197.2 (Jan. 2014), *Homo sapiens* BPI fold containing family B, member 1 (BPIFB1), mRNA. First seen at NCBI on Aug. 6, 2001.
Alimohammadi et al. (Mar. 2009). "Pulmonary autoimmunity as a feature of autoimmune polyendocrine syndrome type 1 and identification of KCNRG as a bronchial autoantigen," Proc Natl Acad Sci U S A. 106(11):4396-401.
Brusko (Apr. 2008). "Clinical application of regulatory T cells for treatment of type 1 diabetes and transplantation," Eur J Immunol. 38(4):931-4.
Chapman (Feb. 2011). Interstitial Lung Disease (Online). Cleveland Clinic Disease Management Project. Retrieved Nov. 7, 2011. Available on the internet: <URL: http://web.archive.org/web/20100210133555/http://www.clevelandclinicmeded.com/medicalpubs/diseasemanagement/pulmonary/interstitial-lung-disease/>.
Devoss et al. (Sep. 2008). "Effector mechanisms of the autoimmune syndrome in the murine model of autoimmune polyglandular syndrome type 1," J Immunol. 181(6):4072-9.
International Search Report for International Application No. PCT/US2011/040060, mailed on Apr. 9, 2012.
Jiang et al. (Jun. 2001). "Total dose and frequency of administration critically affect success of nasal mucosal tolerance induction," Br J Ophthalmol. 85(6):739-44.
Ludvigsson et al. (Oct. 2008). "GAD Treatment and Insulin Secretion in Recent-Onset Type 1 Diabetes," N Engl J Med 359:1909-1920.
Miller (Sep. 2007). "Antigen-specific tolerance strategies for the prevention and treatment of autoimmune disease," Nat Rev Immunol. 7(9):665-77.
Sakaguchi S. (Apr. 2005). "Naturally arising Foxp3-expressing CD25+CD4+ regulatory T cells in immunological tolerance to self and non-self," Nat Immunol. 6(4):345-52.
Smith (Dec. 2006). "Multi-peptide coupled-cell tolerance ameliorates ongoing relapsing EAE associated with multiple pathogenic autoreactivities," J Autoimmun. 27(4):218-31.
Bingle et al. (2011). "Distant cousins: genomic and sequence diversity within the BPI fold-containing (BPIF)/PLUNC protein family," Biochem. Soc. Trans., 39(4):961-965.
Shum et al. (2013). "BPIFB1 is a lung-specific autoantigen associated with interstitial lung disease," Sci. Transl. Med., 5(206):206ra139.

* cited by examiner

*Primary Examiner* — Kevin Hill
(74) *Attorney, Agent, or Firm* — Morrison & Foerster LLP

(57) ABSTRACT

The present disclosure is generally related to pulmonary autoantigens. The disclosure provides methods and kits for assessing whether a subject has or is predisposed to interstitial lung disease. Additionally the present disclosure provides methods of treatment and animal models of interstitial lung disease.

15 Claims, 20 Drawing Sheets

MWVLQALAIMLSIQAGTLDLVETPPVVGNLPVAMPPLNL
PVGGLSPPVLKGPVNHQMLPPKRPVPPPKGGKCPAAR
YFLSSDKLHDYLMSTLPPQIEDMVKCDEVNLEGMLAVLN
TVESSDLLSLLDGISLLKGGEGGGLGIGGLGNEGNGDSS
KPSSGSKATGGLGQLIPGGIPGTEALGGLLNLGDKSSG
KGLLNGDGLSKIKKPLEDAVENVSGIKDAQEKVNEVVPD
GVKEPLNDVLKMDIKDTLLELKVGQVTLDDMEINMEANG
MQVLSMLTATIDGKGVLGPVISLLQFEAKMDVMTTIVAS
NNTQCVNLDAQDTHMHVKEMKIQLVETVTGKVPLPPLP
LDQIIPAIVTAKINENLEKSNSCAIVLNDFNNCKNNGLFSY
QVNTARISPKGLVILYCAKANIGNKTVPVGGRLPPPKN
ASIAVTISSTTLKTLVKEVAKNSSVQMDGLEAQITHIFASQ
ENNTLRVVYKVDITKNGEHFATGETKLFISHGSKISSTLIP
DVKLIRSEHSVVPPEAKEEVEGILSEVGKVAWSNFNTYK
KMNIPVGVSSHTLKNSDVKLMKSIDLQAAS 591 aa

*FIG. 3E*

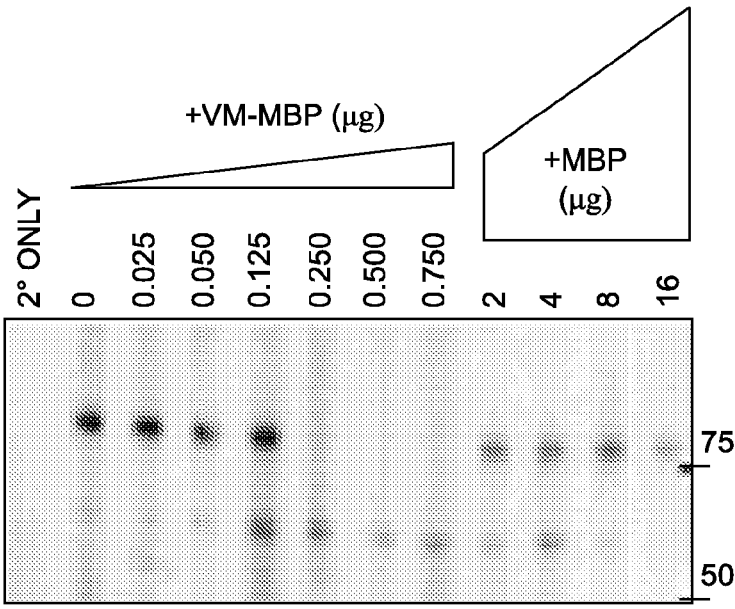

*FIG. 3F*

HEALTHY CONTROL

APS1 WITH LUNG DISEASE

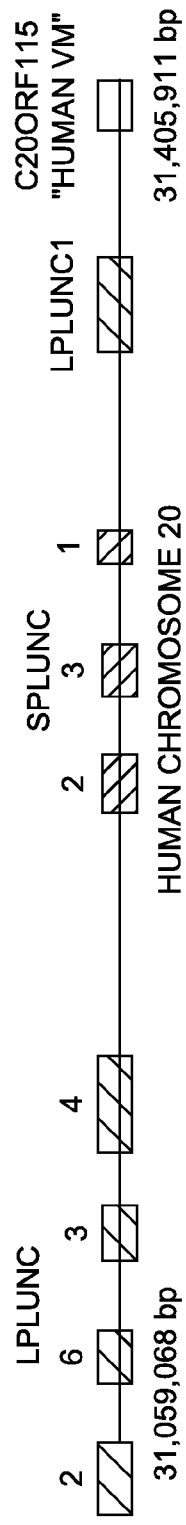
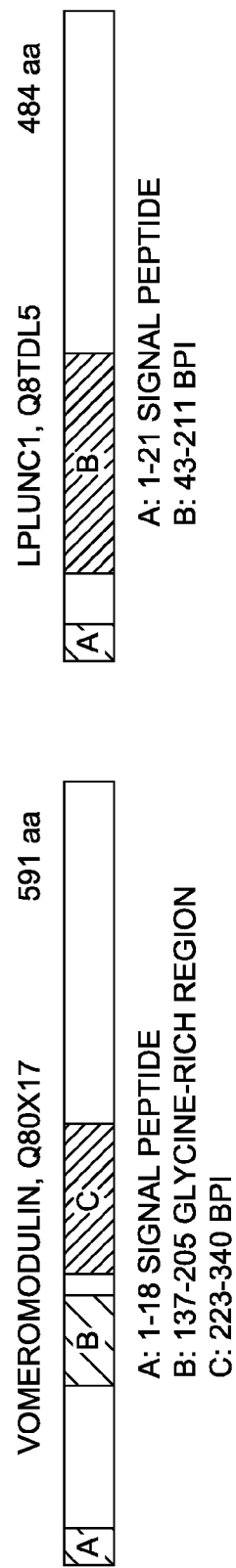
FIG. 9C
FIG. 9D
FIG. 9E

LPLUNC1

SEQUENCE LISTING

```
<160> NUMBER OF SEQ ID NOS: 9

<210> SEQ ID NO 1
<211> LENGTH: 591
<212> TYPE: PRT
<213> ORGANISM: Mus musculus

<400> SEQUENCE: 1

Met Trp Val Leu Gln Ala Leu Ala Ile Met Leu Ser Ile Gln Ala Gly
 1               5                  10                  15

Thr Leu Asp Leu Val Glu Thr Pro Val Val Gly Asn Leu Pro Val
                20                  25                  30

Ala Met Pro Val Pro Leu Asn Leu Pro Val Gly Gly Leu Ser Pro Pro
                35                  40                  45

Val Leu Lys Gly Pro Val Asn His Gln Met Leu Pro Pro Lys Arg Pro
        50                  55                  60

Val Pro Pro Lys Gly Gly Lys Cys Ala Pro Ala Ala Arg Tyr Phe
65                  70                  75                  80

Leu Ser Ser Asp Lys Leu His Asp Tyr Leu Met Ser Thr Leu Pro Pro
                85                  90                  95
```

```
Gln Ile Glu Asp Met Val Lys Cys Asp Glu Val Asn Leu Glu Gly Met
                100                 105                 110
Leu Ala Asp Val Leu Asn Thr Val Glu Ser Ser Asp Leu Leu Ser Leu
            115                 120                 125
Leu Asp Gly Ile Ser Leu Leu Lys Gly Glu Gly Gly Gly Leu Gly
        130                 135                 140
Ile Gly Gly Leu Leu Gly Asn Glu Gly Asn Gly Asp Ser Ser Lys Pro
145                 150                 155                 160
Ser Ser Gly Ser Lys Ala Thr Gly Gly Leu Gly Gln Leu Ile Pro Gly
                165                 170                 175
Gly Ile Pro Gly Thr Glu Ala Leu Gly Gly Leu Leu Asn Leu Gly Gly
            180                 185                 190
Asp Lys Ser Ser Gly Lys Gly Leu Leu Asn Gly Asp Gly Leu Ser Lys
        195                 200                 205
Ile Lys Lys Pro Leu Glu Asp Ala Val Glu Asn Val Ser Gly Ile Lys
210                 215                 220
Asp Ala Ile Gln Glu Lys Val Asn Glu Val Val Pro Asp Gly Val Lys
225                 230                 235                 240
Glu Pro Leu Asn Asp Val Leu Lys Met Asp Ile Lys Asp Thr Leu Leu
                245                 250                 255
Glu Leu Lys Val Gly Gln Val Thr Leu Asp Asp Met Glu Ile Asn Met
            260                 265                 270
Glu Ala Asn Gly Met Gln Val Leu Ser Met Leu Thr Ala Thr Ile Asp
        275                 280                 285
Gly Lys Gly Val Leu Gly Pro Val Ile Ser Leu Leu Gln Phe Glu Ala
290                 295                 300
Lys Met Asp Val Met Thr Thr Ile Ala Val Ala Ser Asn Asn Thr Gln
305                 310                 315                 320
Cys Val Asn Leu Asp Ala Gln Asp Thr His Met His Val Lys Glu Met
                325                 330                 335
Lys Ile Gln Leu Val Glu Thr Val Thr Gly Lys Val Pro Leu Pro Val
            340                 345                 350
Pro Leu Pro Leu Asp Gln Ile Ile Pro Ala Ile Val Thr Ala Lys Ile
        355                 360                 365
Asn Glu Asn Leu Glu Lys Ser Asn Ser Cys Ala Ile Val Leu Asn Asp
370                 375                 380
Phe Asn Asn Cys Lys Asn Asn Thr Gly Leu Phe Ser Tyr Gln Val Asn
385                 390                 395                 400
Thr Ala Arg Ile Ser Pro Lys Gly Leu Val Ile Leu Tyr Cys Ala Lys
                405                 410                 415
Ala Asn Ile Gly Asn Lys Thr Val Pro Val Pro Gly Gly Arg Leu Pro
            420                 425                 430
Pro Asp Pro Lys Asn Ala Ser Ile Ala Val Thr Ile Ser Ser Thr Thr
        435                 440                 445
Leu Lys Thr Leu Val Lys Glu Val Ala Lys Asn Ser Ser Val Gln Met
450                 455                 460
Asp Gly Leu Glu Ala Gln Ile Thr His Ile Ala Phe Ala Ser Gln Glu
465                 470                 475                 480
Asn Asn Thr Leu Arg Val Val Tyr Lys Val Asp Ile Thr Lys Asn Gly
                485                 490                 495
Glu His Phe Ala Thr Gly Glu Thr Lys Leu Phe Ile Ser His Gly Ser
            500                 505                 510
```

```
Lys Ile Ser Asn Ser Thr Leu Ile Pro Asp Val Lys Leu Ile Arg Ser
            515                 520                 525

Glu His Ser Val Val Pro Pro Glu Ala Lys Glu Val Glu Gly Ile
530                 535                 540

Leu Ser Glu Val Gly Lys Val Ala Trp Ser Asn Phe Asn Glu Thr Tyr
545                 550                 555                 560

Lys Lys Met Asn Ile Pro Val Gly Val Ser Ser His Thr Leu Lys Asn
                565                 570                 575

Ser Asp Val Lys Leu Met Lys Ser Ile Asp Leu Gln Ala Ala Ser
            580                 585                 590

<210> SEQ ID NO 2
<211> LENGTH: 484
<212> TYPE: PRT
<213> ORGANISM: Homo sapiens

<400> SEQUENCE: 2

Met Ala Gly Pro Trp Thr Phe Thr Leu Leu Cys Gly Leu Leu Ala Ala
1               5                   10                  15

Thr Leu Ile Gln Ala Thr Leu Ser Pro Thr Ala Val Leu Ile Leu Gly
            20                  25                  30

Pro Lys Val Ile Lys Glu Lys Leu Thr Gln Glu Leu Lys Asp His Asn
        35                  40                  45

Ala Thr Ser Ile Leu Gln Gln Leu Pro Leu Leu Ser Ala Met Arg Glu
    50                  55                  60

Lys Pro Ala Gly Gly Ile Pro Val Leu Gly Ser Leu Val Asn Thr Val
65                  70                  75                  80

Leu Lys His Ile Ile Trp Leu Lys Val Ile Thr Ala Asn Ile Leu Gln
                85                  90                  95

Leu Gln Val Lys Pro Ser Ala Asn Asp Gln Glu Leu Leu Val Lys Ile
            100                 105                 110

Pro Leu Asp Met Val Ala Gly Phe Asn Thr Pro Leu Val Lys Thr Ile
        115                 120                 125

Val Glu Phe His Met Thr Thr Glu Ala Gln Ala Thr Ile Arg Met Asp
    130                 135                 140

Thr Ser Ala Ser Gly Pro Thr Arg Leu Val Leu Ser Asp Cys Ala Thr
145                 150                 155                 160

Ser His Gly Ser Leu Arg Ile Gln Leu Leu His Lys Leu Ser Phe Leu
                165                 170                 175

Val Asn Ala Leu Ala Lys Gln Val Met Asn Leu Leu Val Pro Ser Leu
            180                 185                 190

Pro Asn Leu Val Lys Asn Gln Leu Cys Pro Val Ile Glu Ala Ser Phe
        195                 200                 205

Asn Gly Met Tyr Ala Asp Leu Leu Gln Leu Val Lys Val Pro Ile Ser
    210                 215                 220

Leu Ser Ile Asp Arg Leu Glu Phe Asp Leu Leu Tyr Pro Ala Ile Lys
225                 230                 235                 240

Gly Asp Thr Ile Gln Leu Tyr Leu Gly Ala Lys Leu Leu Asp Ser Gln
                245                 250                 255

Gly Lys Val Thr Lys Trp Phe Asn Asn Ser Ala Ala Ser Leu Thr Met
            260                 265                 270

Pro Thr Leu Asp Asn Ile Pro Phe Ser Leu Ile Val Ser Gln Asp Val
        275                 280                 285

Val Lys Ala Ala Val Ala Ala Val Leu Ser Pro Glu Glu Phe Met Val
    290                 295                 300
```

-continued

```
Leu Leu Asp Ser Val Leu Pro Glu Ala His Arg Leu Lys Ser Ser
305                 310                 315                 320

Ile Gly Leu Ile Asn Glu Lys Ala Ala Asp Lys Leu Gly Ser Thr Gln
                325                 330                 335

Ile Val Lys Ile Leu Thr Gln Asp Thr Pro Glu Phe Phe Ile Asp Gln
                340                 345                 350

Gly His Ala Lys Val Ala Gln Leu Ile Val Leu Glu Val Phe Pro Ser
                355                 360                 365

Ser Glu Ala Leu Arg Pro Leu Phe Thr Leu Gly Ile Glu Ala Ser Ser
370                 375                 380

Glu Ala Gln Phe Tyr Thr Lys Gly Asp Gln Leu Ile Leu Asn Leu Asn
385                 390                 395                 400

Asn Ile Ser Ser Asp Arg Ile Gln Leu Met Asn Ser Gly Ile Gly Trp
                405                 410                 415

Phe Gln Pro Asp Val Leu Lys Asn Ile Ile Thr Glu Ile Ile His Ser
                420                 425                 430

Ile Leu Leu Pro Asn Gln Asn Gly Lys Leu Arg Ser Gly Val Pro Val
                435                 440                 445

Ser Leu Val Lys Ala Leu Gly Phe Glu Ala Ala Glu Ser Ser Leu Thr
450                 455                 460

Lys Asp Ala Leu Val Leu Thr Pro Ala Ser Leu Trp Lys Pro Ser Ser
465                 470                 475                 480

Pro Val Ser Gln

<210> SEQ ID NO 3
<211> LENGTH: 487
<212> TYPE: PRT
<213> ORGANISM: Homo sapiens

<400> SEQUENCE: 3

Met Arg Glu Asn Met Ala Arg Gly Pro Cys Asn Ala Pro Arg Trp Val
1               5                   10                  15

Ser Leu Met Val Leu Val Ala Ile Gly Thr Ala Val Thr Ala Ala Val
                20                  25                  30

Asn Pro Gly Val Val Arg Ile Ser Gln Lys Gly Leu Asp Tyr Ala
                35                  40                  45

Ser Gln Gln Gly Thr Ala Ala Leu Gln Lys Glu Leu Lys Arg Ile Lys
            50                  55                  60

Ile Pro Asp Tyr Ser Asp Ser Phe Lys Ile Lys His Leu Gly Lys Gly
65              70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
                100                 105                 110

Asn Ala Asn Ile Lys Ile Ser Gly Lys Trp Lys Ala Gln Lys Arg Phe
            115                 120                 125

Leu Lys Met Ser Gly Asn Phe Asp Leu Ser Ile Glu Gly Met Ser Ile
130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
                180                 185                 190
```

```
Ile Glu Ser Ala Leu Arg Asn Lys Met Asn Ser Gln Val Cys Glu Lys
        195                 200                 205
Val Thr Asn Ser Val Ser Ser Lys Leu Gln Pro Tyr Phe Gln Thr Leu
    210                 215                 220
Pro Val Met Thr Lys Ile Asp Ser Val Ala Gly Ile Asn Tyr Gly Leu
225                 230                 235                 240
Val Ala Pro Pro Ala Thr Thr Ala Glu Thr Leu Asp Val Gln Met Lys
            245                 250                 255
Gly Glu Phe Tyr Ser Glu Asn His His Asn Pro Pro Phe Ala Pro
            260                 265                 270
Pro Val Met Glu Phe Pro Ala Ala His Asp Arg Met Val Tyr Leu Gly
        275                 280                 285
Leu Ser Asp Tyr Phe Phe Asn Thr Ala Gly Leu Val Tyr Gln Glu Ala
        290                 295                 300
Gly Val Leu Lys Met Thr Leu Arg Asp Asp Met Ile Pro Lys Glu Ser
305                 310                 315                 320
Lys Phe Arg Leu Thr Thr Lys Phe Phe Gly Thr Phe Leu Pro Glu Val
                325                 330                 335
Ala Lys Lys Phe Pro Asn Met Lys Ile Gln Ile His Val Ser Ala Ser
            340                 345                 350
Thr Pro Pro His Leu Ser Val Gln Pro Thr Gly Leu Thr Phe Tyr Pro
        355                 360                 365
Ala Val Asp Val Gln Ala Phe Ala Val Leu Pro Asn Ser Ser Leu Ala
        370                 375                 380
Ser Leu Phe Leu Ile Gly Met His Thr Thr Gly Ser Met Glu Val Ser
385                 390                 395                 400
Ala Glu Ser Asn Arg Leu Val Gly Glu Leu Lys Leu Asp Arg Leu Leu
                405                 410                 415
Leu Glu Leu Lys His Ser Asn Ile Gly Pro Phe Pro Val Glu Leu Leu
                420                 425                 430
Gln Asp Ile Met Asn Tyr Ile Val Pro Ile Leu Val Leu Pro Arg Val
        435                 440                 445
Asn Glu Lys Leu Gln Lys Gly Phe Pro Leu Pro Thr Pro Ala Arg Val
    450                 455                 460
Gln Leu Tyr Asn Val Val Leu Gln Pro His Gln Asn Phe Leu Leu Phe
465                 470                 475                 480
Gly Ala Asp Val Val Tyr Lys
                485

<210> SEQ ID NO 4
<211> LENGTH: 23
<212> TYPE: DNA
<213> ORGANISM: Artificial Sequence
<220> FEATURE:
<223> OTHER INFORMATION: Synthetic Construct

<400> SEQUENCE: 4
tcagcttgct gcctgaaggt caa                                         23

<210> SEQ ID NO 5
<211> LENGTH: 17
<212> TYPE: DNA
<213> ORGANISM: Artificial Sequence
<220> FEATURE:
<223> OTHER INFORMATION: Synthetic Construct

<400> SEQUENCE: 5
```

```
tcagcttgct gcctgaa                                                              17

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

<400> SEQUENCE: 6
cgaattctca gcttgctgcc tgaaggtcaa                                                30

<210> SEQ ID NO 7
<211> LENGTH: 25
<212> TYPE: DNA
<213> ORGANISM: Artificial Sequence
<220> FEATURE:
<223> OTHER INFORMATION: Synthetic Construct

<400> SEQUENCE: 7
atgtcgactc agcttgctgc ctgaa                                                     25

<210> SEQ ID NO 8
<211> LENGTH: 15
<212> TYPE: PRT
<213> ORGANISM: Mus musculus

<400> SEQUENCE: 8

Asn Leu Glu Gly Met Leu Ala Asp Val Leu Asn Thr Val Glu Ser
 1               5                  10                  15

<210> SEQ ID NO 9
<211> LENGTH: 17
<212> TYPE: PRT
<213> ORGANISM: Gallus gallus domesticus

<400> SEQUENCE: 9

Ile Ser Gln Ala Val His Ala Ala His Ala Glu Ile Asn Glu Ala Gly
 1               5                  10                  15

Arg
```

BIOMARKERS ASSOCIATED WITH AUTOIMMUNE DISEASES OF THE LUNG

CROSS-REFERENCE TO RELATED APPLICATIONS

This application is a U.S. National Phase of PCT/US2011/040060, filed Jun. 10, 2011, which claims the benefit under 35 USC 119(e) of U.S. Provisional Patent Application No. 61/354,184, filed Jun. 11, 2010, each of which is incorporated herein by reference in its entirety for all purposes.

STATEMENT REGARDING FEDERALLY SPONSORED RESEARCH OR DEVELOPMENT

This invention was made with government support under Grant Nos. AI035297, DK59958, EY016408, and T32 HL007185 awarded by the National Institutes of Health. The government has certain rights in the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 643662001200SeqList.txt, date recorded: Dec. 7, 2012, size: 14 KB).

FIELD

The present disclosure is generally related to pulmonary autoantigens. The disclosure provides methods and kits for assessing whether a subject has or is predisposed to interstitial lung disease. Additionally the present disclosure provides methods of treatment and animal models of interstitial lung disease.

BACKGROUND

Current methods for the treatment of autoimmune diseases of the lung rely on powerful immunosuppressive medications with significant systemic side effects. But validated lung-specific autoantigens, which may facilitate the diagnosis and treatment of autoimmune-mediated lung diseases, are currently unknown.

Therefore, a significant biomedical need exists for the identification of lung autoantigens and methods of their use as prognostic or diagnostics biomarkers for autoimmune diseases of the lung. A need also exists for antigen-specific therapies for autoimmune disease of the lung, such as interstitial lung disease.

SUMMARY

The present disclosure is generally related to pulmonary autoantigens. The disclosure provides methods and kits for assessing whether a subject has or is predisposed to interstitial lung disease. Additionally the present disclosure provides methods of treatment and animal models of interstitial lung disease.

In particular, the disclosure provides diagnostic and prognostic tests for interstitial lung diseases (ILD) by quantifying antibody or T-cell mediated immune responses to a pulmonary autoantigen (e.g., antigen expressed in the lung that has at least one bactericidal/permeability-increasing protein (BPI) domain. In some embodiments, the methods involve assessing whether a mammalian patient has or is predisposed to an interstitial lung diseases (ILD), comprising: a) subjecting a biological sample from the patient to a procedure for quantitation of an immune response to a lung autoantigen, wherein the lung autoantigen comprises at least one bactericidal/permeability-increasing protein (BPI) domain, and wherein the procedure comprises an antibody-based assay or a T cell-based assay; and b) detecting an elevated immune response to the lung autoantigen in the biological sample as compared to a control biological sample, wherein the elevated immune response is associated with presence of the ILD or a predisposition to ILD. Preferred examples of such lung autoantigens include long palate, lung, and nasal epithelium carcinoma-associated protein 1 (LPLUNC1), LPLUNC1-like proteins, vomeromodulin, and vomeromodulin-like proteins. Lung autoantigens of this disclosure may be measured in a biological sample including but not limited to blood, plasma, serum, bronchial alveolar lavage (BAL) fluid, and lung tissue. In some embodiments, the ILD is idiopathic ILD or connective tissue disease associated ILD. Patients subjected to the methods may have or may be suspected of having a systemic autoimmune disease, such as rheumatoid arthritis, scleroderma, sjogren's syndrome, systemic lupus erythematosis, sarcoidosis, wegener's granulomatosis, or autoimmune polyendocrine syndrome type 1 (APS-1).

One aspect of the disclosure provides an antibody-based assay for measurement of lung autoantigen-reactive antibodies present in the biological samples of the patient for use in the methods of a preceding paragraph. Exemplary antibody-based assays include ELISA, Western blotting, immunofluoresence analysis, flow cytometry, and antibody microarray. Additionally kits for use in the antibody-based methods are provided. In some embodiments, the kits comprise a first reagent that specifically binds to the lung autoantigen-reactive antibodies, and a second reagent for detecting the antibodies, wherein the first reagent is the lung autoantigen or a cell expressing the lung autoantigen, and the second reagent comprises a secondary antibody that is reactive with constant regions of the lung autoantigen-reactive antibodies of the mammalian subject.

Another aspect of the disclosure provides a T cell-based assay for measurement of lung autoantigen-reactive T lymphocytes present in the biological sample of the patient for use in the methods of a preceding paragraph. Exemplary T cell-based assays include cytokine ELISA, ELISPOT analysis, flow cytometry, and proliferation assay. Additionally, kits for use in the T cell-based methods are provided. In some embodiments, the kits comprise a first reagent that specifically activates the lung autoantigen-reactive T lymphocytes, and a second reagent for detecting the activated T lymphocytes, wherein the first reagent comprises the lung autoantigen or a peptide derived therefrom, and the second reagent comprises thymidine.

Moreover the present disclosure provides methods that further comprise one or more additional steps. In some embodiments, the methods of a preceding paragraph further comprise performing one or both of a pulmonary function test and a high resolution computed tomography scan on the patient. In some embodiments, the methods of a preceding paragraph further comprising: c) administering a treatment to the patient when the elevated immune response is detected. In one aspect, the treatment comprises one of the group consisting of a corticosteroid, cyclophosphamide, mycophenolate mofetil, and azathioprine. In another aspect the treatment comprises an antigen-specific tolerance regimen. In some embodiments, the treatment comprises a mucosal tolerance regimen comprising dispensing a formulation to the patient by an oral or an intra-nasal route, wherein the formulation comprises a pharmaceutically acceptable excipient, and an effective amount of the lung autoantigen, or a peptide derived therefrom. In some embodiments, the treatment comprises a parenteral tolerance regimen comprising dispensing a formulation to the patient by intravenous or subcutaneous injection, wherein the formulation comprises an effective amount of the lung autoantigen, a peptide derived therefrom, or a nucleic acid encoding the lung autoantigen in operable combination with a regulatory sequence. In some embodiments, the treatment comprises an antigen-coupled cell tolerance regimen comprising dispensing a formulation to the patient by intravenous injection, wherein the formulation comprises an effective amount of the lung autoantigen, or a peptide derived therefrom, wherein the autoantigen or the peptide is coupled to ethylene carbodiimide-fixed, autologous antigen presenting cells. In some embodiments, the treatment comprises a regulatory T cell regimen comprising dispensing a formulation to the patient by intravenous injection, wherein the formulation comprises an effective amount of ex vivo-expanded lung autoantigen-specific regulatory T cells.

The disclosure further provides an animal model of interstitial lung disease comprising a mammal immunized with a formulation comprising an adjuvant and a lung autoantigen comprising at least one bactericidal/permeability-increasing protein (BPI) domain. In one aspect, the lung autoantigen is a long palate, lung, and nasal epithelium carcinoma-associated protein 1 (LPLUNC1) or a LPLUNC1-like protein. In one aspect, the autoantigen is vomeromodulin or a vomeromodulin-like protein. In one aspect the mammal is selected from the group consisting of rodents, dogs, cows, and non-human primates. In one aspect the mammal is a mouse or a rat.

BRIEF DESCRIPTION OF THE DRAWINGS

FIG. 3 demonstrates that vomeromodulin (VM) is the predominant antigen targeted in lungs of Aire$^{o/o}$ mice. FIG. 3E depicts the amino acid sequence of the 80 kD spot, indicating that it is vomeromodulin (SEQ ID NO:1). The cDNA of vomeromodulin is set forth as GENBANK Accession No. NM_001025574.1. Identified peptides, were mapped onto the VM amino acid sequence and revealed coverage of nearly the entire protein. FIG. 3F shows a competition blot, which was to confirm autoantibody reactivity to VM. The blot showed that 80 kD reactivity was abolished after addition of recombinant VM-MBP. The MBP tag alone failed to abolish reactivity.

FIG. 5 shows T cells with specificity for vomeromodulin in Aire$^{o/o}$ mice.

FIG. 6 illustrates the induction of lung-specific disease by breaking tolerance to vomeromodulin in wild-type mice.

FIG. 8 illustrates the lung-specific disease phenotype observed after adoptive transfer of VM-specific T cells.

FIG. 9 documents autoreactivity to a human bronchial epithelial protein, LPLUNC1, in a patient with APS1 and lung disease. FIG. 9A shows an immunofluorescence stain of normal frozen human lung with serum from an APS1 patient with lung disease, whereas FIG. 9C reviews the genomic organization of the human VM pseudogene locus (C20orf115) and shows the adjacent human PLUNC gene family with individual genes numbered as indicated. FIG. 9D illustrates the domain structure of the murine vomeromodulin protein showing the BPI domain. FIG. 9E illustrates the domain structure of human LPLUNC1, also including a BPI domain.

DEFINITIONS

Figure 1A:
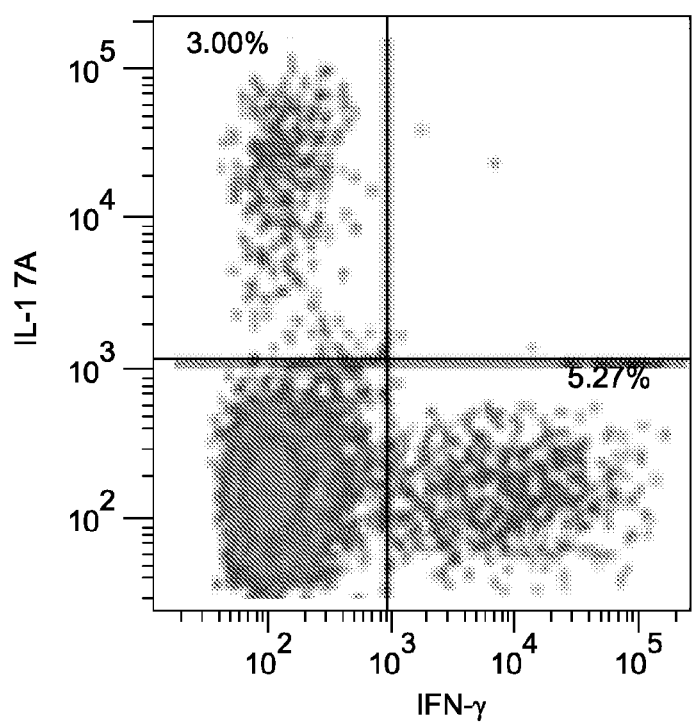
FIG. 1A depicts a representative plot of CD4$^+$ lung lymphocytes from a BALB/c Aire$^{o/o}$ mouse at 14 weeks, showing IL-17A, IFN-γ, IL-4 and IL-10 containing cells. The right panel shows percentages of total CD4$^+$ lung lymphocytes producing cytokines averaged from 5 BALB/c Aire$^{o/o}$ mice aged 12-16 weeks. Data are mean±SEM.
Figure 1A:
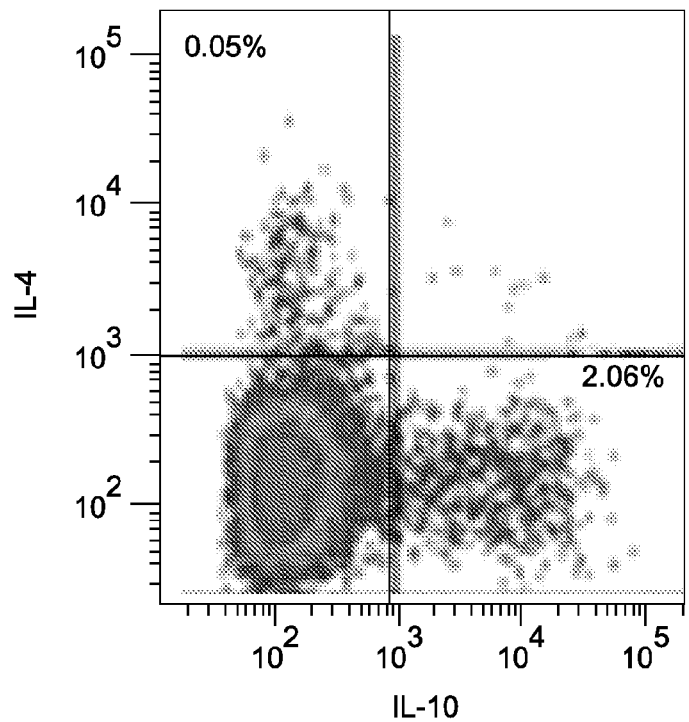
Figure 1A:
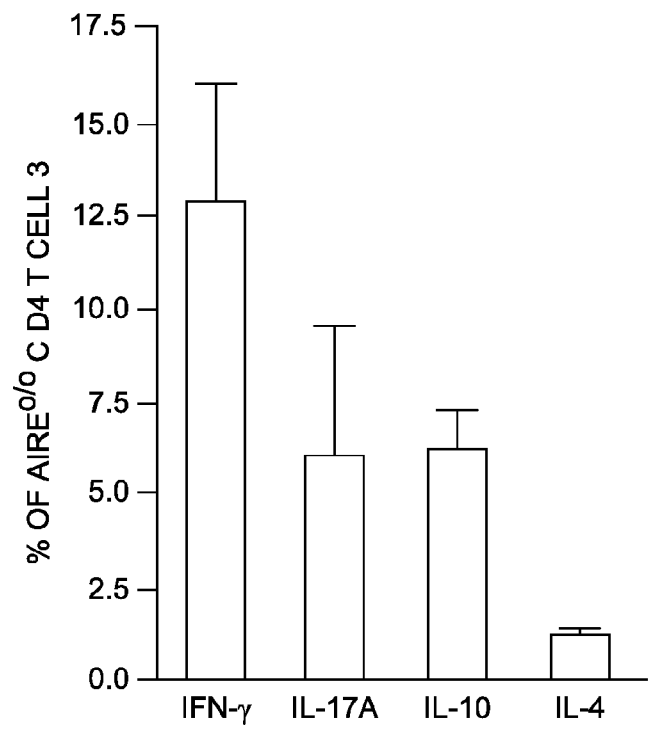

To facilitate an understanding of the embodiments disclosed herein, a number of terms and phrases are defined below.

The terms "interstitial lung disease" and "ILD" as used herein refer to a group of lung diseases affecting the interstitium (the tissue and space around air sacs of the lungs). ILDs affect areas in the lung comprising the alveolar epithelium, pulmonary capillary endothelium, basement membrane, perivascular and perilymphatic tissues. The term ILD is used to distinguish these diseases from obstructive airways diseases.

The term "predisposed to" as used herein in connection with a disease, refers to an increased statistical likelihood that test subjects having a specific phenotype, such as an elevated immune response to an antigen, will develop the disease as compared to control subjects that do not possess the specific phenotype.

The terms "bacterial/permeability-increasing protein," "BPI," "lipopolysaccharide-binding protein," "LBP," "cholesteryl ester transfer protein," and "CETP" as used herein refer to a human antigen, as well as its cDNA and genomic DNA, and mammalian counterparts thereof. The cDNA sequence of human BPI is provided by GENBANK Accession No. AX752831.1. The amino acid sequence of human BPI is provided below as SEQ ID NO:3

```
MRENMARGPCNAPRWVSLMVLVAIGTAVTAAVNPGVVVRISQKGLDYASQQGTAAL

QKELKRIKIPDYSDSFKIKHLGKGHYSFYSMDIREFQLPSSQISMVPNVGLKFSISNANIKI

SGKWKAQKRFLKMSGNFDLSIEGMSISADLKLGSNPTSGKPTITCSSCSSHINSVHVHISK

SKVGWLIQLFHKKIESALRNKMNSQVCEKVTNSVSSKLQPYFQTLPVMTKIDSVAGINY

GLVAPPATTAETLDVQMKGEFYSENHHNPPPFAPPVMEFPAAHDRMVYLGLSDYFFNT

AGLVYQEAGVLKMTLRDDMIPKESKFRLTTKFFGTFLPEVAKKFPNMKIQIHVSASTPP

HLSVQPTGLTFYPAVDVQAFAVLPNSSLASLFLIGMHTTGSMEVSAESNRLVGELKLDR

LLLELKHSNIGPFPVELLQDIMNYIVPILVLPRVNEKLQKGFPLPTPARVQLYNVVLQPH

QNFLLFGADVVYK.
```

As used herein, the term "BPI domain" refers to a structural unit within a larger polypeptide, which shares its three dimensional architecture and at least 40% amino acid sequence identity with a family of secretary proteins having antimicrobial activity. The human BPI protein has two BPI domains: BPI1 from residues 35 to 260; and BPI2 from residues 284 to 484. The conserved domain search (CD-Search) of the National Center for Biotechnology Information (NCBI) using default parameters can be used to determine whether the amino acid sequence of a protein of interest possesses a BPI domain (Marchler-Bauer and Bryant, Nucleic Acids Res, 32(W)327-331, 2004; and Marchler-Bauer et al., Nucleic Acids Res, 37(D)205-10, 2009).

The terms "long palate, lung and nasal epithelium carcinoma-associated protein 1," "LPLUNC1," "von Ebner minor salivary gland protein," "VEMSGP" and "c20orf114" as used herein refer to a human pulmonary antigen, as well as its cDNA and genomic DNA, and mammalian counterparts thereof. LPLUNC1 is thought to play a role in the innate immune response to bacterial exposure in the mouth, nasal cavities and lungs. The cDNA sequence of human LPLUNC1 is provided by GENBANK Accession No. NM_033197.2. The amino acid sequence of human LPLUNC1 is provided below as SEQ ID NO:2: MAGPWTFTLLCGL-LAATLIQATLSPTAVLILGPKVIKEKLTQELKDHNA-TSILQQLPLLS AMREKPAGGIPVLGSLVNTVLKHII-WLKVITANILQLQVKPSANDQELLVKIPLDMVAG FNTPLVKTIVEFHMTTEAQATIRMDTSASGPTRLVLS-DCATSHGSLRIQLLHKLSFLVNA LAKQVMNLLVPSL-PNLVKNQLCPVIEASFNGMYADLLQLVKVPISLSI-DRLEFDLLYPAI KGDTIQLYLGAKLLDSQGKVTKW-FNNSAASLTMPTLDNIPFSLIVSQDVVKAAVAAVL SPEEFMVLLDSVLPESAHRLKSSIGLINEKAADKLG-STQIVKILTQDTPEFFIDQGHAKVA QLIVLEVFPS-SEALRPLFTLGIEASSEAQFYTKGDQLILNLNNI-SSDRIQLMNSGIGWFQPD VLKNIITEIIHSILLPN-QNGKLRSGVPVSLVKALGFEAAESSLT-KDALVLTPASLWKPSSP VSQ. As used herein, the term "LPLUNC1-like protein" refers to members of the PLUNC superfamily. In preferred embodiments, LPLUNC-1 like proteins are at least 70% identical to the amino acid sequence of SEQ ID NO:2.

The terms "vomeromodulin" and "VM" as used herein refer to mouse pulmonary antigen, as well as its cDNA and genomic DNA, and mammalian counterparts thereof. The cDNA sequence of mouse vomeromodulin is provided by GENBANK Accession No. NM_001025574.1. The amino acid sequence of mouse vomeromodulin is provided below as SEQ ID NO:1: MWVLQALAIMLSIQAGTLDLVETPPV-VGNLPVAMPVPLNLPVGGLSPPVLKGPVNHQM LPP-KRPVPPPKGGKCAPAARYFLSSDKLH-DYLMSTLPPQIEDMVKCDEVNLEGMLADV LNTVESSDLLSLLDGISLLKGGEGGGL-GIGGLLGNEGNGDSSKPSSGSKATGGLGQLIPG GIPGTEALGGLLNLGGDKSS-GKGLLNGDGLSKIKKPLEDAVENVSGIK-DAIQEKVNEVV PDGVKEPLNDVLKMDIKDTL-LELKVGQVTLDDMEINMEANGMQVLSMLTATIDGKGV LGPVISLLQFEAKMDVMTTIA-VASNNTQCVNLDAQDTHMHVKEMKIQL-VETVTGKVP LPVPLPLDQIIPAIVTAKINENLEKSN-SCAIVLNDFNNCKNNTGLFSYQVNTARISPKGLVI LYCAKANIGNKTVPVPGGRLPPDPKNA-SIAVTISSTTLKTLVKEVAKNSSVQMDGLEAQ ITHI-AFASQENNTLRVVYKVDITKNGEHFAT-GETKLFISHGSKISNSTLIPDVKLIRSEHSV VPPEAKEEVEGILSEVGKVAWSNFNE-TYKKMNIPVGVSSHTLKNSDVKLMKSIDLQAA S. As used herein, the term "vomeromodulin-like protein" refers to proteins that are at least 70% identical to the amino acid sequence of SEQ ID NO:1.

The terms "autoimmune polyendocrine syndrome type 1" and "APS-1" as used herein refers to an autosomal recessive autoimmune disease phenotype caused by a defect in the AutoImmune Regulator (AIRE) transcription factor.

The term "pulmonary function test" as used herein refers to any diagnostic test, such as spirometry, or medical examination designed to assess the functional integrity of the lung. Typically, such tests comprise determinations of the volume of air that can be inhaled and exhaled and the rates of the respective airflow.

The term "high resolution computer tomography" as used herein refers to a medical imaging technology for the non-invasive diagnosis of living human or animal subjects, wherein the technology provides a three-dimensional representation of the organs in question and allows for the determination of the organs' anatomical and functional integrity.

The term "animal model" as used herein refers to a non-human animal that mimics a human disease phenotype in the sense that treatment measures which remedy the disease phenotype in the non-human animal can also remedy the disease phenotype in human patients.

The term "adjuvant" as used herein refers to a composition that acts to facilitate a specific antibody based and/or cell based immune response against an antigen without itself being a specific target of the immune response.

The term "elevated level" as used herein in connection to an immune response, refers to an antigen-specific antibody and/or T cell response (e.g., vomeromodulin or LPLUNC1 reactive immune responses) in a biological sample that is at least 2.5-fold greater than the level of the immune response to the antigen in a control sample. In some embodiments, an elevated level is at least 2.5, 2.6, 2.7, 2.8, 2.9, 3.0, 3.1, 3.2, 3.3, 3.4, 3.5, 4.0, 4.5, 5.0, 6.0, 7.0, 8.0, 9.0, or 10-fold greater.

As used herein the term "antibody-based assay" refers to any technique that involves the use of an antibody to detect an antigen. Such techniques include but are not limited to immunostaining, ELISA, antibody microarray, flow cytometry, and Western blotting.

As used herein the term "cell-based assay" refers to any technique that involves the measurement of antigen-specific T lymphocytes. Such techniques include but are not limited to ELISPOT assays, proliferation assays, and MHC-peptide tetramer staining.

As used herein, the term "microscopy-based assay" refers to any technique that involves the use of a microscope to assess a phenotype of a cell or tissue.

DETAILED DESCRIPTION

The present disclosure is generally related to pulmonary autoantigens. The disclosure provides methods and kits for assessing whether a subject has or is predisposed to interstitial lung disease. Additionally the present disclosure provides methods of treatment and animal models of interstitial lung disease.

The lung is often damaged in systemic autoimmune diseases such as rheumatoid arthritis and scleroderma. One of the most common pulmonary manifestations of systemic autoimmune syndromes is interstitial lung disease (ILD). This term comprises a heterogeneous group of disorders in which fibrosis and inflammation occur within alveolar walls or in the loose tissue surrounding peribronchovascular sheaths, interlobular septa and the visceral pleura. An alternative form of interstitial lung disease is idiopathic ILD, which occurs in the absence of an autoimmune syndrome and instead arises as an isolated pulmonary process.

The AIRE-deficient model of autoimmunity. Human subjects with defects in the autoimmune regulator (AIRE) develop Autoimmune Polyglandular Syndrome Type 1

(APS1), a multi-organ autoimmune disease that involves the lung in some subjects. AIRE is expressed primarily within the thymus in thymic medullary epithelial cells (mTECs). AIRE promotes immune tolerance by driving the ectopic expression of a wide array of organ specific self-antigens in mTECs. In the absence of appropriate AIRE expression, these self-antigens are not displayed in the thymus, leading to a defect in thymic deletion of autoreactive T cells. The multi-organ nature of disease in AIRE-deficient animals is viewed as a result of the spectrum of self-antigens whose thymic expression relies on AIRE. Aire-deficient mice (Aire$^{o/o}$) develop lung autoimmunity that is strikingly similar in pattern to the disease reported in APS1 patients, but the specificity of this response was unknown.

Several important findings were made relating to the lung-specific autoimmune reactivity observed in Aire$^{o/o}$ mice and human APS1 patients. First, vomeromodulin was identified as the predominant lung-specific autoantigen in Aire$^{o/o}$ mice Immunoblots using lung lysate prepared from immunodeficient SCID mice and probed with serum from Aire$^{o/o}$ mice demonstrated the presence of autoantibodies in Aire$^{o/o}$ mice that specifically targeted vomeromodulin (VM), a 80 kD lung protein. VM was located on the surface of the bronchiolar epithelium. It was shown to be secreted into the airway and detectable in BAL fluid from the lung by immunoblotting. No other lung autoantigens besides VM were identified, demonstrating that VM is the primary lung antigen in Aire$^{o/o}$ mice. Importantly, recombinant VM protein was shown to neutralize autoreactive antibodies found in Aire$^{o/o}$ mice, suggesting a therapeutic utility for purified VM. Additionally, Aire$^{o/o}$ mice were shown to have autoreactive T cells that specifically respond to VM and that either the adoptive transfer of VM reactive T cells into SCID mice or the immunization of wild type mice with purified VM can cause lung-specific autoimmune disease phenotypes. These experiments therefore demonstrated that the lung-specific autoantigen VM alone can act as a disease causing agent. The neutralization of cellular and antibody based autoimmune reactivity against VM can therefore be of therapeutic use in the treatment of lung-specific autoimmune diseases and aid in the development of Aire$^{o/o}$ mice as an animal model for pharmacological research.

The human homolog of mouse VM was determined to be a pseudogene, which is not expressed in human APS1 patients. Nevertheless, the organization of the human genomic region surrounding this pseudogene is similar to the genomic organization around mouse VM and comprises coding sequences for PLUNC proteins. Specifically, LPLUNC1 is encoded in a region immediately adjacent to the human VM pseudogene. Like VM, LPLUNC1 is highly expressed in the bronchial epithelium of the human lung and serum of a human APS1 patient was successfully used to stain LPLUNC1 in lung tissue obtained from a normal control specimen. The pattern of immunoreactivity was nearly identical to the pattern of staining seen using sera from Aire$^{o/o}$ mice. This data shows that the lung disease in an APS1 patient closely recapitulates the lung disease in Aire$^{o/o}$ mice, suggesting that LPLUNC1 is an important human lung autoantigen.

Prognostic and Diagnostic Methods

In one embodiment, patients at risk of or suspected of having ILD and having an elevated immune response to a lung autoantigen (pulmonary antigen such as PLUNC1, which comprises at least one BPI domain) are identified as having or being predisposed to ILD. In some embodiments, the patient has a systemic autoimmune disease. In some embodiments, the methods are performed on more than one occasion in order to assess a patient's response to therapy or to assess a patient's prognosis.

In one embodiment, background immune response to the lung autoantigen in normal subjects are established to define an 'elevated' immune response level of expression of the marker. Depending on the technique used and the immune response examined, different values may be used to define an 'elevated' immune response to the lung autoantigen. In order to define an 'elevated' immune response, statistical analysis may be used.

Antibody Based Methods

In some embodiments, an elevated antibody response to a lung autoantigen (pulmonary antigen such as PLUNC1, which comprises at least one BPI domain) in a biological sample from a patient is detected. Antibody-based methods include various techniques that involve the measurement of lung autoantigen (pulmonary antigen such as PLUNC1, which comprises at least one BPI domain)-reactive antibodies. Commonly used antibody-based techniques to detect the level of a humoral immune response of a patient include but are not limited to ELISA, Western blotting, immunofluorescence analysis, flow cytometry, and antibody microarray.

T Cell-Based Methods

In some embodiments, an elevated T cell responses to a lung autoantigen (pulmonary antigen such as PLUNC1, which comprises at least one BPI domain) in a biological sample from a patient is detected. T Cell-based methods include various techniques that involve the measurement of T cell activation by the lung autoantigen. Commonly used T cell-based techniques to detect the level of a cellular immune response of a patient include but are not limited to proliferation assays, and cytokine secretion assays (e.g., ELISA, ELISPOT, etc.). Cytokines that are frequently used to assay T cell activation include but are not limited to IL-2, and interferon-gamma.

Treatment Methods

In yet another embodiment, when an elevated immune response to a lung autoantigen (e.g., pulmonary antigen such as PLUNC1, which comprises at least one BPI domain) is detected in a biological sample from a patient as compared to that measured in a control biological sample, treatment of the patient is indicated. For instance, in some embodiments, upon detection of an elevated immune response to a lung autoantigen (pulmonary antigen such as PLUNC1, which comprises at least one BPI domain) a non-specific immunosuppressive treatment or an lung autoantigen-specific tolerance regimen is administered. Suitable non-specific immunosuppressive treatments include but are not limited to corticosteroid, cyclophosphamide, mycophenolate mofetil, azathioprine, and mTOR inhibitor (e.g., rapamycin). In some preferred embodiments, the lung autoantigen is in the form of a soluble protein, a protein fixed to an antigen presenting cell, a soluble peptide, a peptide fixed to an antigen presenting cell or a peptide presented by a soluble MHC multimer. Suitable antigen-specific tolerance regimens include but are not limited to mucosal tolerance, parenteral tolerance, and antigen-coupled cell tolerance regimens (See, e.g., Miller et al., Nature Reviews Immunology, 7:665-677, 2007; and Ludvigsson et al., N Engl J Med, 359:19019-1920, 2008). Alternatively, a regulatory T cell regimen is employed, which involves the ex vivo expansion of autologous lung autoantigen-specific regulatory T cells.

Kits

In another embodiment, a kit comprising a lung autoantigen (pulmonary antigen such as PLUNC1, which comprises at least one BPI domain) is provided. In some embodiments, the kit further comprises a reagent for detecting antibody binding to the lung autoantigen. In other embodiments, the kit further comprises a reagent for detecting activation of T lymphocytes by the lung autoantigen. Reagents capable of detecting antibody binding are typically directly or indirectly linked to a tag such as a radiolabel, a chromophore, a fluorophore or an enzyme that catalyzes a reaction resulting in a detectable signal. Reagents capable of detecting activation of T lymphocytes by the lung autoantigen also typically comprise a tag.

EXAMPLES

The present disclosure is described in further detail in the following examples, which are not in any way intended to limit the scope of the disclosure as claimed. The attached figures are meant to be considered as integral parts of the specification and description of the disclosure. The following examples are offered to illustrate, but not to limit the claimed disclosure.

In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); OD (optical density); PCR (polymerase chain reaction); and RT-PCR (reverse transcription PCR). Additional abbreviations include: BAL (bronchoalveolar lavage) fluid; BPI (bacterial permeability-increasing protein); LPLUNC (long palate, lung and nasal epithelium carcinoma-associated protein); MHC (major histocompatibility complex); Th (helper T lymphocyte); and VM (vomeromodulin).

Example 1

Lung-Specific Biomarkers for the Diagnosis and Treatment of Autoimmune Disease

This example provides a description of the materials and methods and results of analyses of the role of vomeromodulin and LPLUNC1 as predominant antigens in autoimmune diseases of the lung.

Materials and Methods

Mice: $Aire^{o/o}$ mice were generated as described (1, 2). $Aire^{o/o}$ mice used in these experiments were backcrossed into the C57BL/6, BALB/c, and NOD ShiLt/J backgrounds >10 generations. BALB/c SCID mice were purchased from the Jackson Laboratory. All mice were housed in a pathogen-free barrier facility at UCSF. Experiments complied with the Animal Welfare Act and NIH guidelines for the ethical care and use of animals in biomedical research and were approved by the UCSF Animal Care and Use Committee.

Histology: Organs from mice were harvested and fixed overnight in 10% formalin, embedded in paraffin, sectioned, and stained for hematoxylin and eosin. Human specimens were stained by the UCSF Pathology Laboratory Immune infiltrates of organs were confirmed by an independent reading of the slides with a blinded observer.

Lung histology scoring system: Lung histology sections were scored based on the following grading system: grade 0, normal lung; grade 1, infrequent perivascular and peribronchiolar mononuclear infiltrates; grade 2, frequent perivascular and peribronchiolar mononuclear infiltrates; grade 3, dense perivascular and peribronchiolar mononuclear infiltrates and interstitial pneumonia; grade 4, diffuse perivascular and peribronchiolar mononuclear infiltrates, interstitial pneumonia and architectural distortion.

Immunostaining: Immune cell subtypes were visualized by immunohistochemistry using antibodies specific for CD4, CD8, and B220 (BD Biosciences) and a DAB staining kit (Vector Laboratories) on 7-micron frozen sections of $Aire^{o/o}$ mice cut on a cryostat. The human lung tissue biopsy was stained by the UCSF Pathology Laboratory.

Indirect immunofluorescence: Seven-micron frozen sections from SCID mice and a lung tissue sample provided by the UCSF Pathology Department taken from a patient who expired of non-pulmonary disease were fixed and blocked in PBS containing 1% bovine serum albumin and 3% serum from same species as the secondary antibody, overnight at 4° C. Primary incubation with mouse sera was at 1:100 for an hour and goat anti-mouse FITC (Jackson Immunoresearch) was used at 1:1000 for an hour. Primary incubation using human sera was at 1:100 for an hour and secondary incubation with donkey anti-human FITC (Jackson Immunoresearch) was at 1:2000 for an hour. An anti-LPLUNC1 antibody (Abnova, No. H00092747-B01P) was used at 1:100 and incubated for an hour and goat anti-mouse FITC (Jackson Immunoresearch) was used at 1:1000 for an hour. Slides were examined on a microscope (Axiostar; Carl Zeiss MicroImaging, Inc.) with 5", 10", 20" and 40" lenses. Images were obtained using an AxioCam with AxioVision software (both from Carl Zeiss MicroImaging, Inc.).

Flow cytometry: Lungs were minced and then digested in 2 mg/ml collagenase Dulbecco's Modified Eagle Medium (DMEM) for 20 minutes. The remaining tissue was dispersed by vortexing and filtered through nylon mesh. Cells were placed in DMEM complete media with 10% FCS and Golgi-Stop (BD Biosciences) and stimulated with 10 ng/ml phorbol 12-myristate 13-acetate (PMA) and 0.5 µM ionomycin (Sigma-Aldrich) for 4 h at 37° C. After the incubation, cells were surface stained with antibodies specific for CD4, CD8, and CD45 to be able to sort lymphocytes, then permeabilized and stained with antibodies specific for IL-4, IL-10, IL-17A, IFN-γ, or isotype control (BD Biosciences). Cells were analyzed on a LSRII flow cytometer (BD Biosciences) (3).

Immunoblotting: Sera were screened for the presence of autoantibodies by immunoblotting as described (2). Sera from BALB/c, B6 and NOD $Aire^{o/o}$ and $Aire^{+/+}$ mice were used at a 1:600 dilution and incubated overnight. The secondary antibody was peroxidase-conjugated goat antibody to mouse IgG (Jackson Immunoresearch) used at 1:20,000 on immunoblots (1:15,000 on multiscreen immunoblots) for 1 hr. For competition studies, sera were pre-incubated with serial dilutions of recombinant VM-MBP or MBP overnight at 4° C. The anti-VM sera were used at 1:200 for 1 hr, and a peroxidase-conjugated goat antibody to rabbit IgG secondary antibody was used at 1:10,000 for 1 hr. For the multi-organ blot protein loading control, a GAPDH antibody (Santa Cruz Biotech) was used at 1:1000, and a peroxidase-conjugated goat antibody to mouse IgG secondary (Jackson Immunoresearch) antibody was used at 1:2000 for 1 hr. Tissue lysates were prepared in 0.1% CHAPS buffer from frozen organs harvested from immunodeficient SCID mice.

Immunoaffinity purification: Immunoprecipitation of the VM autoantigen was performed with Aire$^{o/o}$ sera as described (2). The autoantigen was isolated from BAL fluid obtained by lavaging with PBS the lungs of several perfused and bled SCID mice. Protein agarose A/G beads (1:1 ratio) were covalently coupled to $Aire^{o/o}$ serum that had known reactivity to the 80 kD protein and placed into a column. The columns were washed in 30 mL PBS, and BAL was passed through the matrix. Columns were washed with 30 mL PBS and washed again with 30 mL of 10 mM phosphate, pH 6.8. Column elutions were collected by passing 0.5 ml fractions of 100 mM glycine, pH 2.5, over the column and collecting the flow-through. Elutions from multiple runs were pooled and concentrated in a centrifugal protein concentrator (Sartorius). The isolated protein was run out on a pH 3-10, non-linear two-dimensional gel in MOPS buffer, coomassie stained and the excised spots were sent for peptide mass spectrometry analysis.

Preparation of cDNA from organs and RT-PCR: RNA from organs was prepared according to manufacturer's instructions with an RNA isolation kit (Stratagene). RNA was reverse transcribed into cDNA using Superscript III (Invitrogen) and poly-dT primers and the VM and cyclophilin cDNA was amplified for 35 cycles. The following VM primers were used: forward 5'-TCA GCT TGC TGC CTG AAG GTC AA-3' (SEQ ID NO:4); and reverse 5'-TCA GCT TGC TGC CTG AA-3' (SEQ ID NO:5).

Real-time PCR: Real-time PCR was performed on cDNA prepared from DNase-treated RNA. Aire, insulin2, GAD67 and cyclophilin primers were used as described (2). For VM, we used the ABI Taqman Gene Expression Assay kit (Applied Biosystems No. Mm00723516_m1). Reactions were run on a sequence detection system machine (HT7900; Applied Biosystems). For the analysis of target gene expression from thymic stromal cDNA, the standard curve method was used.

Fusion protein vectors: Recombinant proteins were produced by cloning full length cDNA sequences into the pMAL-C2X system. Lung cDNA was prepared as above. The VM primers used to generate the full length cDNA with restriction sites for subcloning were: forward 5'-CGA ATT CTC AGC TTG CTG CCT GAA GGT CAA-3' (SEQ ID NO:6); and reverse 5'-ATG TCG ACT CAG CTT GCT GCC TGA A-3' (SEQ ID NO:7). PCR products were subcloned into pMAL-C2X via restriction digestion, ligated and transformed into BL-21 bacteria for protein expression; protein was harvested according to the manufacturer's instructions (pMAL system, New England Biolabs).

Prediction and selection of VM peptides: An online computer program was used that relies on Average Relative Binding (ARB) matrices to predict peptide sequences that bind to MHC molecules (4). H-2 $IA^d$ was selected as the matrix platform, the predicted $IC_{50}$ function was set as linear and the $IC_{50}$ (nM) cut off value was set at 5000.

ELISPOT analysis: $CD4^+$ T cells from $Aire^{o/o}$ or $Aire^{+/+}$ mice BALB/c mice were isolated by cell sorting on a cytometer (MoFlo; Dako). The release of IFN-γ by $CD4^+$ T cells was measured by ELISPOT assay. In brief, plates (Immunospot M200; BD Biosciences) were coated with 2 μg/ml of anti-mouse IFN-γ mAb (BD Biosciences) and incubated overnight at 4° C. The plates were washed with PBS and blocked with DMEM containing 10% FCS for 2 h at 37° C. The CD4+ T cells and irradiated APCs from syngeneic mice were plated at a ratio of 1:4 and VM-MBP and MBP proteins added. The plates were incubated for 24 hrs at 37° C. in 10% $CO_2$ incubator. At the completion of the incubation, the plates were washed thoroughly with PBS before adding 2 μg/ml of biotin-labeled IFN-γ mAb (2 μg/ml; BD Biosciences) and incubating for 2 hrs at 4° C. After further incubation with avidin-horseradish peroxidase (1:100 dilutions; BD Biosciences) for 1 h at room temperature, the plates were developed using substrate solution (BD Biosciences). Positive spots in the plate membranes were examined using an ELISPOT reader system (Transtec; Cell Technology). The number of spot-forming cells was the average number of spots in duplicate wells.

Immunization: Six to 8 week old BALB/c $Aire^{+/+}$ mice were immunized subcutaneously on the back in 4 spots with 100 μg of VM-MBP or MBP in an emulsion of 100 μL CFA supplemented with mycobacterium tuberculosis H37RA (4 mg/uL), using a modified EAE protocol (5). Re-immunizations using 100 μg of VM-MBP or MBP in 100 μL IFA were given 1 and 4 weeks after first immunization. Mice were sacrificed 4 weeks after the last immunization and the organs analyzed for histology.

Adoptive transfer of VM specific T cells: BALB/c $Aire^{+/+}$ mice were immunized with 100 μg VM-111 (NLEGMLADVLNTVES set forth as SEQ ID NO:8) or the chicken ovalbumin peptide 323-339 (ISQAVHAAHAEINEAGR set forth as SEQ ID NO:9) mixed in complete Freund's adjuvant (CFA) in 4 different spots on the back. Ten days after immunization, lymph nodes and spleen were harvested. Cells were activated in vitro with 5 μg/mL of peptide in DMEM complete containing 10% FCS. After 4 days, lymphocytes were harvested by density centrifugation gradient and $20\times10^6$ cells in PBS were transferred into each 6-8 week old BALB/c SCID mouse via tail vein injection.

Statistics: Data was analyzed with Prism software (GraphPad) using unpaired t-tests with a two-tailed 95% confidence interval and $P\leq0.05$ considered significant.

Generation of $^{35}$S-Radiolableled VM, LPLUNC and KCNRG- and autoantibody assay: We used full-length cDNA clones for VM (isolated as above), human LPLUNC1 (C20orf114, ATCC No. MGC-14597) and KCNRG (ATCC No. MGC-40406) for in vitro transcription and translation and labeling with $^{35}$S-methionine using the TNT system kit (Promega). The $^{35}$S-radiolabeled proteins immunoprecipitated with serum or positive control antibodies to LPLUNC1 (Abnova No. H00092747-B01P, Sigma No. HPA024256) were aliquoted in triplicate in 96-well PVDF filtration plates (Millipore). In each well, 20,000 counts per minute (cpm) of $^{35}$S-proteins were used for immunoprecipitation. The radioactivity of the immunoprecipitated material was evaluated with the use of a liquid scintillation counter (Beckman Coulter). The autoantibody index was calculated as follows: [cpm in the unknown sample—cpm in the negative standard] ÷[cpm in the positive standard−cpm in the negative standard]×100).

Human subjects: All patients and controls were included in the study only after we had obtained informed written consent. The study protocol was reviewed and approved by the institutional review board at UCSF.

Proliferation measurements by thymidine incorporation: Lymphocytes were harvested from spleen and lymph nodes of peptide-immunized mice (see above) and cultured with 5 μg/mL of either VM-111 or OVA 323-339 peptide, for 4 days in humidified 37° C., 10% $CO_2$ incubator. Cultures were pulsed with 1.0 μCi of [$^3$H] thymidine at 18 hours before termination of culture, harvested using an automated multi-wall harvester and counted using a scintillation counter.

Glycosidase Treatment: BAL fluid from SCID lungs lavaged with PBS was treated with N-Glycosidase F according to the manufacturer's protocol (New England Biolabs, No. P0704L).

Mass spectrometry (MS): Protein samples excised from the gel were directly submitted to the Stanford University Protein and Nucleic Acid facility for mass mapping where the samples were subjected to tryptic digestion and mass analysis of the resulting peptides. Mass mapping was performed on an Applied Biosystems 4700 Proteomics Analyzer, a MALDI mass spectrometer that provides tandem (MS/MS) time-of-flight (TOF) optics to provide peptide structural information, in addition to high-accuracy MS data (6).

Results and Discussion

Interstitial lung disease in Aire$^{o/o}$ mice and an APS1 patient. In order to determine the pattern of lung disease in Aire$^{o/o}$ mice BALB/c, NOD and C57BL/6 (B6) Aire$^{o/o}$ and Aire$^{+/+}$ mice were sacrificed at various ages. The lungs were analyzed for histology by hematoxylin and eosin (H&E) staining. At early ages, the histologic pattern of disease was identical in mice in all strains. The infiltrates were comprised of mononuclear cells in a peribronchovascular distribution. Older BALB/c and NOD mice developed progressive and often severe disease. The mononuclear infiltrates extended into the lung parenchyma and resulted in a temporally homogeneous, mild to moderate cellular interstitial pneumonia that often reached the pleural surface. A prior study reported that lung disease could be induced by the adoptive transfer of Aire$^{o/o}$ splenocytes into immunodeficient SCID mice suggesting that the pulmonary infiltrates are autoimmune in nature (19).

APS1 patients can develop an autoimmune lung disease that is pathologically similar to the infiltrates in the mice (12). The histologic lung pathology Aire$^{o/o}$ mice was compared to a lung biopsy specimen from a patient with APS1 and a history of pulmonary disease. The human lung biopsy demonstrated mononuclear infiltrates surrounding small and medium sized airways similar to infiltrates in Aire$^{o/o}$ mice. The H&E stains also revealed a cellular interstitial pneumonia that mirrored findings in older NOD and BALB/c Aire$^{o/o}$ mice. Stains for acid fast bacilli, bacteria and fungal elements were negative. These results demonstrated that Aire$^{o/o}$ mice exhibit a bronchiolitis that in older NOD and BALB/c Aire$^{o/o}$ animals progresses to a cellular interstitial pneumonia. This histopathology is similar to that in the biopsy from the APS1 subject with pulmonary disease.

Next the lung infiltrating and disease causing cells were identified. To this end, lungs from Aire$^{o/o}$ mice were prepared as frozen sections and immunohistochemistry staining was performed. Within the peribronchovascular infiltrates, the cells stained primarily for CD4, although B cells (indicated by B220 staining) were also present in significant numbers. Several mice with severe disease developed organized lymphoid structures resembling bronchus-associated lymphoid tissue (BALT). This finding is consistent with reports identifying BALT in settings of chronic inflammation, including autoimmune disease (20). The majority of cells residing within the pulmonary interstitium were CD4$^+$ cells, while CD8$^+$ cells were present at lower numbers Immunohistochemistry of tissue sections from the APS1 patient revealed an early germinal center with a significant number of CD20$^+$ B cells. CD4$^+$ cells appeared slightly more abundant than the CD8$^+$ cells.

Figure 2A:
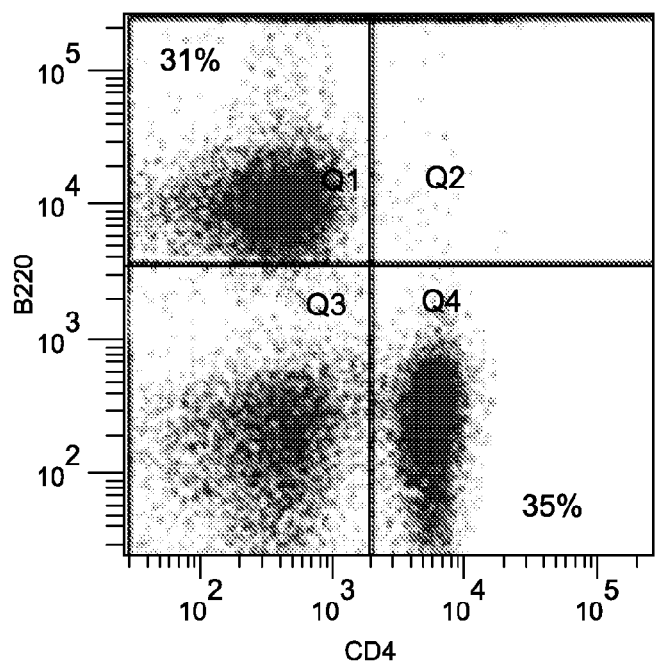
FIG. 2 characterizes lung lymphocytes in Aire$^{0/0}$ mice. The representative FACS plot is gated on lung lymphocytes from a NOD Aire$^{0/0}$ mouse at 10 weeks. Similar percentages were seen in both younger and older mice, as well as in BALB/c Aire$^{0/0}$ mice.
Figure 2B:
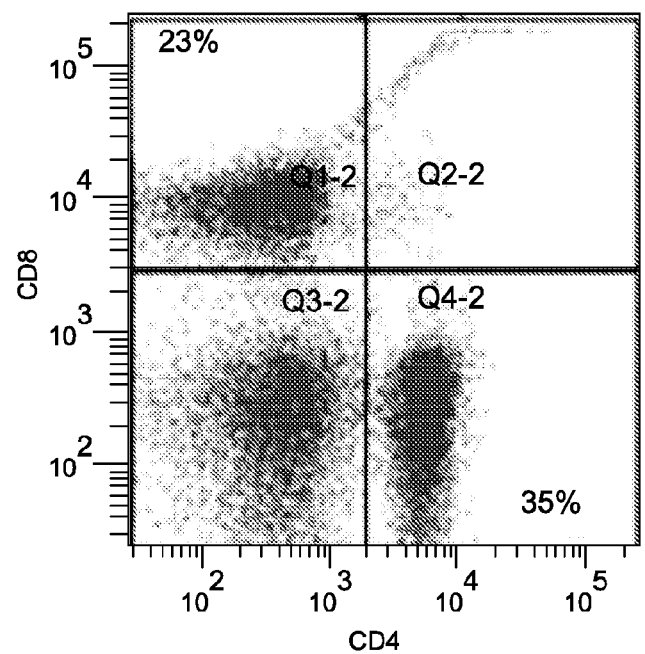

Further characterization of the mouse cells by intracellular cytokine staining was performed to determine the effector mechanisms important for inducing lung disease. Lymphocytes from lungs of BALB/c and NOD Aire$^{o/o}$ mice were stimulated with phorbol 12-myristate 13-acetate (PMA) and ionomycin and analyzed by flow cytometry. The cell counts confirmed that the majority of cells were CD4$^+$ T cells with B cells present in significant numbers (FIG. 2). The predominant effector cytokine produced by Aire$^{o/o}$ lung CD4$^+$ T cells was interferon γ (IFN-γ), followed by roughly equivalent levels of IL-17A and IL-10, and low amounts of IL-4 secreting cells (FIG. 1A). These results show that lung infiltrating cells in Aire$^{o/o}$ mice are primarily TH1 polarized CD4$^+$ T cells, although TH17 and TH2 cells are also present.

The predominance of lymphocytes within the lung parenchyma raised the question whether Aire$^{o/o}$ mice exhibited a lung-specific immune response. Serum from Aire$^{o/o}$ mice with lung disease was used to stain frozen lung sections from immunodeficient SCID mice to determine whether there was autoantibody reactivity to a lung protein. Reactivity was seen on the surface of the bronchiolar epithelium (FIG. 1B); less abundant staining occurred within cells located in the alveoli. Thus, Aire$^{o/o}$ mice develop ILD with a histopathologic pattern similar to that seen in an APS1 patient. The lung infiltrates in Aire$^{o/o}$ mice are comprised of TH1 polarized CD4$^+$ T cells, with some cells skewed toward a TH17 phenotype. Aire$^{o/o}$ mice harbor autoantibodies that target lung proteins located in the bronchiolar epithelium and alveolar cells, indicating a lung-specific immune response.

Figures 3A, 3B:
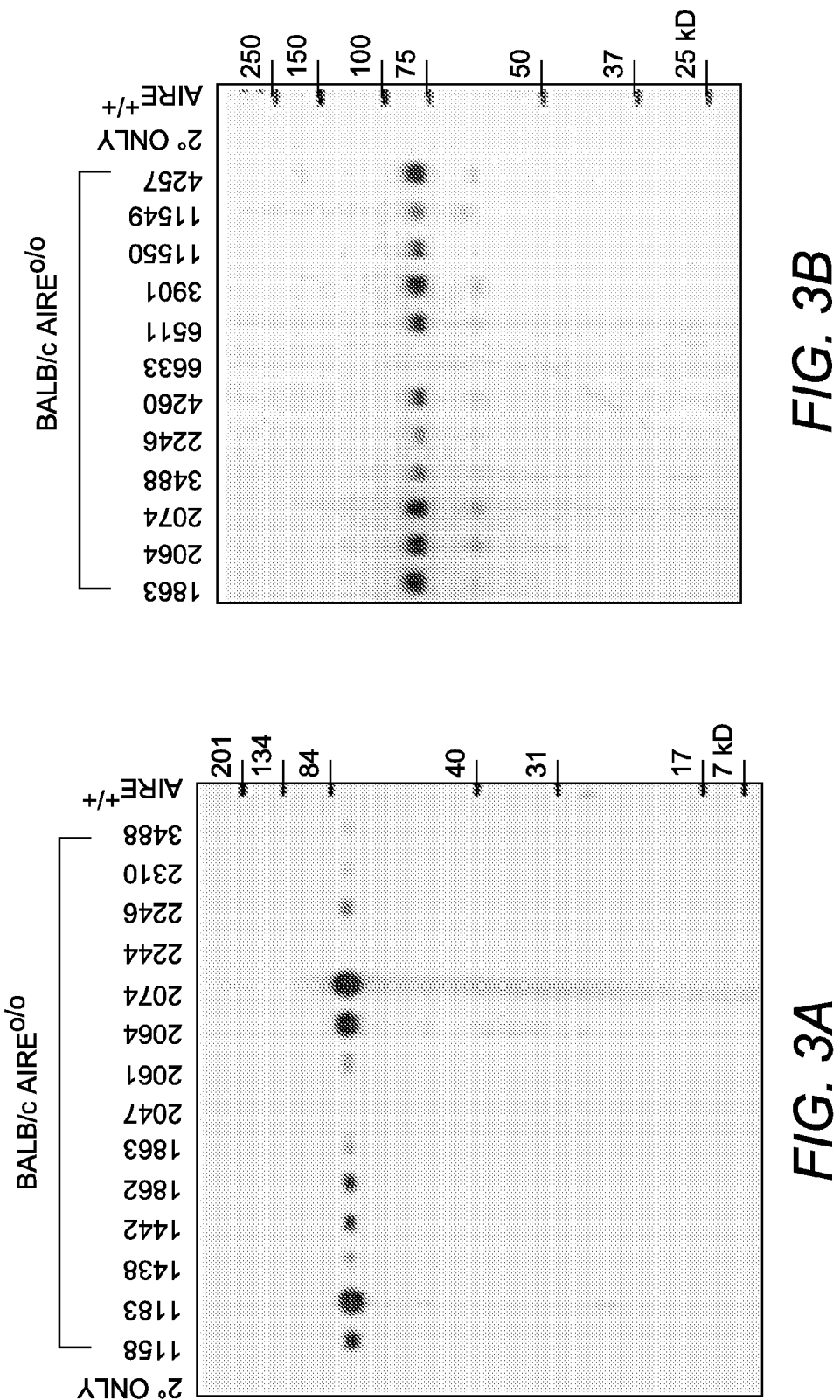
FIG. 3A shows an immunoblot of whole lung lysate probed with sera from BALB/c Aire$^{o/o}$ mice aged 8-20 weeks, the individual animals are numbered. The blot revealed an 80 kD antigen target.
FIG. 3B depicts an immunoblot of BAL fluid probed with sera from BALB/c Aire$^{o/o}$ mice, which also revealed the 80 kD antigen.

Vomeromodulin as a major lung autoantigen in Aire$^{o/o}$ mice Immunoblots were performed using lung lysate prepared from immunodeficient SCID mice and these bolts were subsequently probed with serum from B6, BALB/c and NOD Aire$^{o/o}$ mice. All strains of Aire$^{o/o}$ mice had serum autoantibodies to an 80 kD lung protein, whereas serum from Aire$^{+/+}$ mice did not (FIG. 3A). Immunofluorescence staining using Aire$^{o/o}$ serum (FIG. 1B) revealed that this target antigen was located on the surface of the bronchiolar epithelium. To determine whether the protein was secreted into the airway and whether it was present in BAL fluid from the lung immunoblots were performed of BAL fluid and probed with serum from Aire$^{o/o}$ mice. The blots revealed that the 80 kD antigen was indeed present in BAL fluid (FIG. 3B).

Figure 3C:
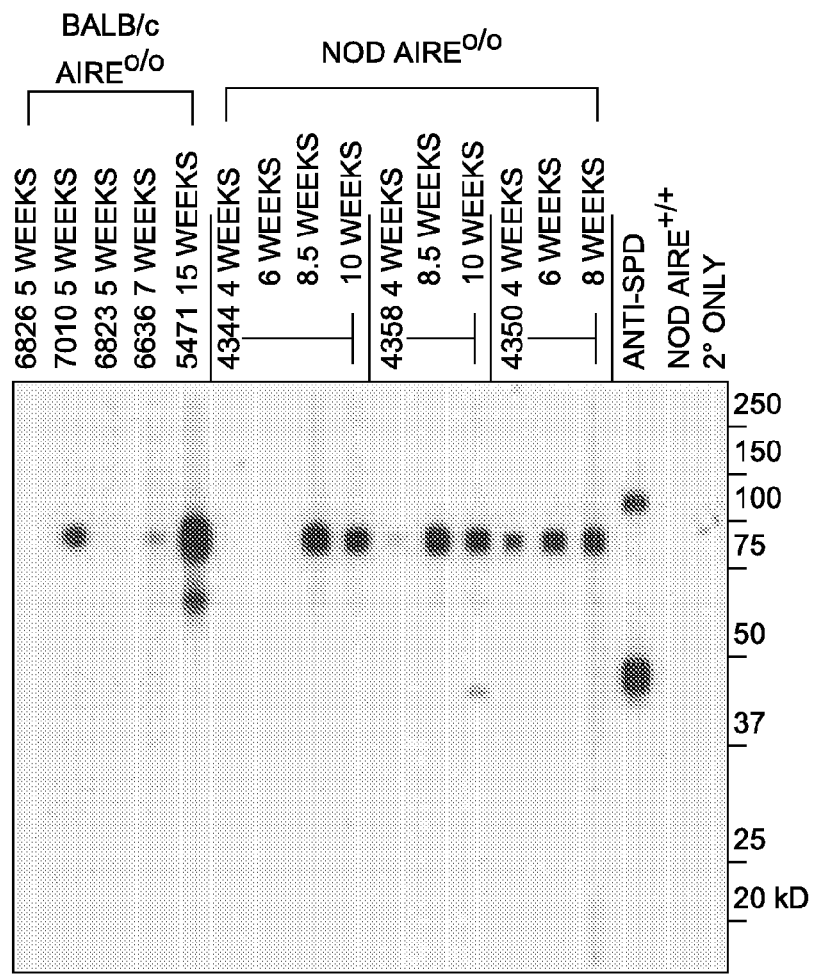
FIG. 3C depicts an immunoblot of BAL fluid probed with NOD mice bled serially and BALB/c mice sacrificed at various ages.

To determine whether other antigens were targeted during the course of disease, sera were tested from NOD Aire$^{o/o}$ mice that were serially bled over 4 to 10 weeks, and BALB/c Aire$^{o/o}$ mice aged 5 to 15 weeks. The 80 kD band was the predominant target, with rare evidence of other immunoreactivity, even in older animals (FIG. 3C). Taken together, these results demonstrate that the 80 kD lung protein is likely a primary lung antigen in Aire$^{o/o}$ mice in all strains.

Figure 3D:
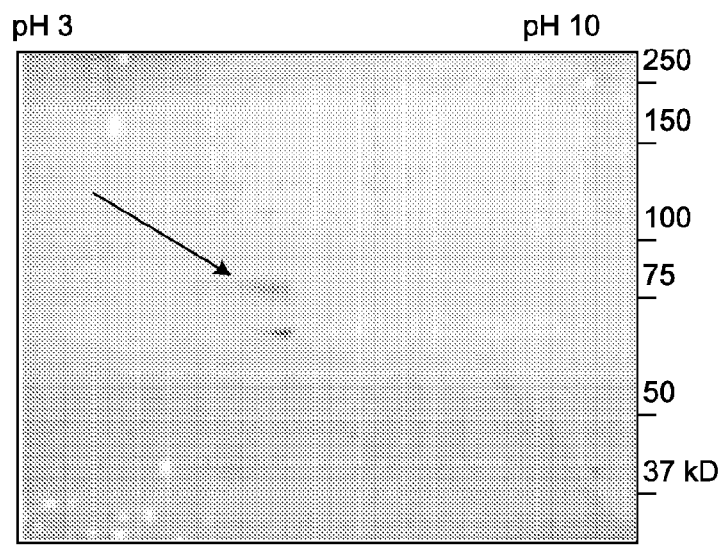
In FIG. 3D sera from Aire$^{o/o}$ mice were used to immunoprecipitate the antigen from BAL fluid, which was then run on a Coomassie-stained 2D gel. Three spots at 80 kD migrated near an isoelectric point ~5.5, as indicated by the arrow. All spots were analyzed by mass spectrometry.
Figure 4:
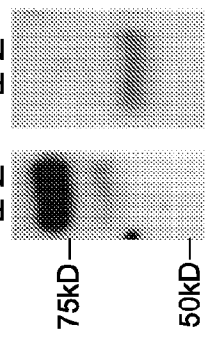
FIG. 4 shows an immunoblot of vomeromodulin after treatment with N-glycosidase. The immunoblot of BAL fluid was probed with NOD Aire$^{0/0}$ mouse serum before and after treatment with N-glycosidase. The amount of post-treatment BAL analyzed was ~1.55 of the pre-treatment protein.

Identification of the 80 kD lung protein targeted in Aire$^{o/o}$ mice. The 80 kD target antigen was immunopurified from BAL fluid, concentrated and resolved on a two-dimensional gel and stained it with coomassie. Four spots were detected, three of which migrated at 80 kD, and an additional spot at 60 kD (FIG. 3D). All four spots were analyzed by mass spectrometry. Peptide mapping from two of the three spots isolated at 80 kD spanned the entire amino acid sequence and were provisionally identified as vomeromodulin (UniProt accession Q80XI7-1) with a high degree of confidence (FIG. 3E). The discrepancy between the predicted molecular weight of vomeromodulin (VM) at 62 kD and the protein on immunoblots at 80 kD appears to be due to glycosylation, which causes VM to migrate at a higher molecular weight (FIG. 4). The 60 kD spot was identified as albumin, which is abundant in BAL fluid and probably non-specifically bound to our immunoprecipitation column.

Figure 3G:
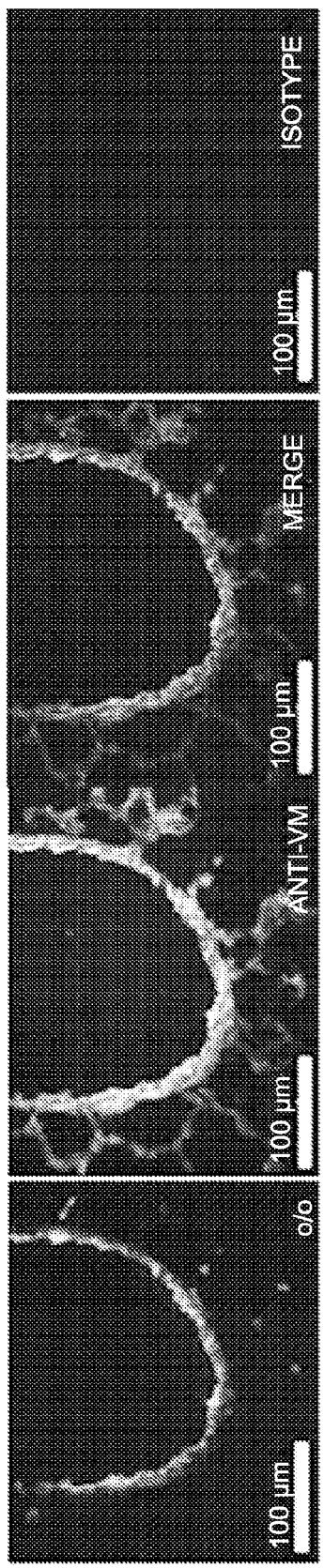
FIG. 3G shows the staining of the apical surface of the bronchiolar epithelium and to rare cells within lung alveoli with both Aire$^{o/o}$ serum and a rat VM anti-serum.

To confirm that the provisional identification of vomeromodulin corresponded to the 80 kD protein on immunoblots, a recombinant VM protein was generated and coupled to a maltose binding protein (MBP) tag. A competition assay performed using recombinant VM (VM-MBP) revealed that the 80 kD serum reactivity on immunoblots was abolished with the addition of 0.25 μg of recombinant protein. As a control, up to 16 μg of the MBP tag were added to the same serum, but these failed to abrogate the 80 kD reactivity (FIG. 3F). Further verification that VM was the target antigen came from co-staining experiments with Aire$^{o/o}$ serum and a rat VM anti-serum. (The sequence identity between rat and mouse VM amino acid sequences is greater than 80%). Merged images of staining with the two antibodies showed they co-localized to the apical surface of the bronchiolar epithelium and to rare cells within lung alveoli (FIG. 3G). In summary, vomeromodulin was identified as the major lung autoantigen in Aire$^{o/o}$ mice, confirming the presence of a lung autoimmune response in this model.

Figure 5A:
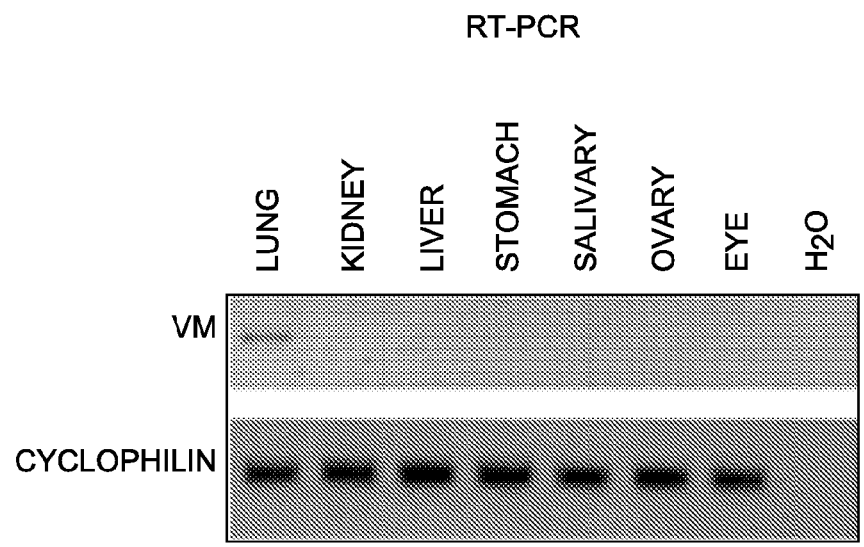
FIG. 5A shows a RT-PCR of vomeromodulin cDNA after 35 cycles in indicated tissues. The RT-PCR revealed a band at expected size of 1.8 kb in lung only. The DNA band was excised and sequenced, confirming that full length VM cDNA was amplified.
Figure 5B:
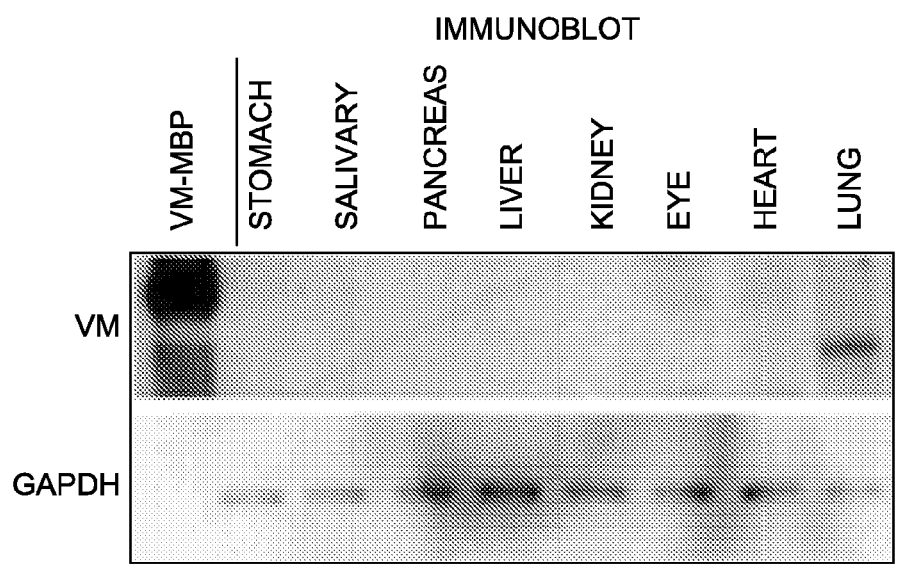
FIG. 5B shows an immunoblot using BALB/c Aire$^{o/o}$ serum to probe tissue lysates of indicated organs and recombinant VM-MBP. Reactivity to the 80 kD band was only seen in lung lysate. Reactivity to VM-MBP occurred at the expected weight of 100 kD.

Aire$^{o/o}$ mice have T cells specific for the Aire-regulated protein vomeromodulin. Vomeromodulin is enriched in the respiratory epithelium of the rat (21). To clarify the tissue distribution of VM in the mouse, RT-PCRs for full length VM cDNA were performed on cDNA libraries of several tissues. VM cDNA could only be amplified from lung cDNA (FIG. 5A). The PCR product was excised and DNA sequencing confirmed the presence of the full coding region of VM. To determine the tissue content of the VM protein, immunoblots were performed on protein lysates of different organs (FIG. 5B). The tissues were probed with a serum sample that had proven reactivity to vomeromodulin as demonstrated through competition immunoblots (FIG. 3F). In the multi-organ immunoblot, the 80 kD reactivity was detected only in lung lysate. Taken together, these data confirm that mouse VM has a restricted expression pattern that is mainly limited to the respiratory epithelium.

Figure 5C:
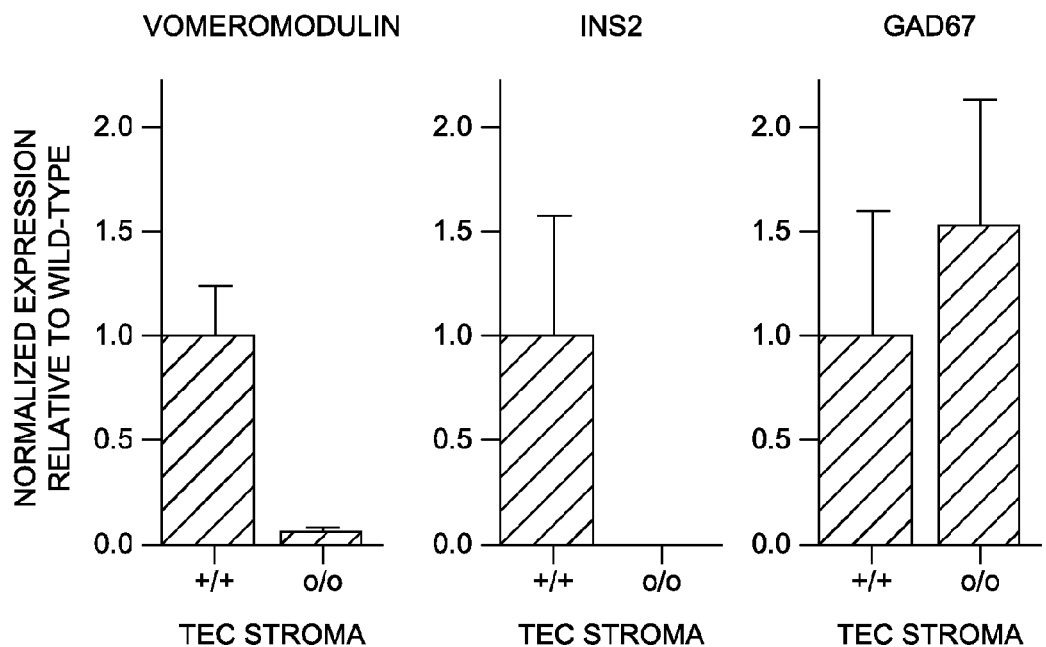
FIG. 5C shows representative results from two independent experiments in which TEC stroma from Aire$^{o/o}$ and Aire$^{+/+}$ thymi was assayed in quadruplicate for VM, insulin 2 (Ins2) and glutamic acid decarboxylase 67 (GAD67) by real-time PCR; data are normalized expression relative to wild-type±SD.
Figure 5D:
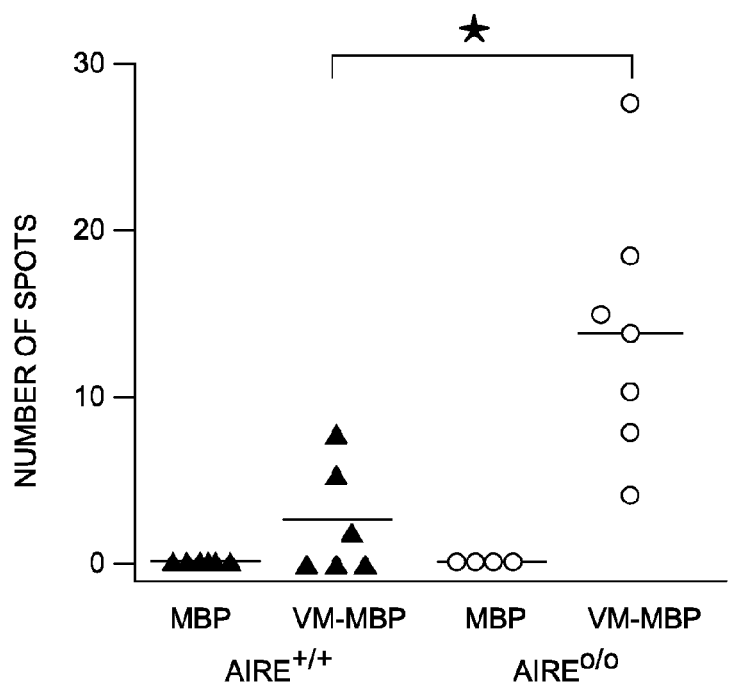
FIG. 5D shows an ELISPOT analysis of IFN-γ producing T cells in Aire$^{o/o}$ and Aire$^{+/+}$ BALB/c mice aged 10-14 weeks (*P=0.005). The Y axis indicates number of spots per 10,000 T cells.

VM is expressed in the thymus in an Aire-dependent manner. Aire$^{o/o}$ mice generate a VM-specific immune response and exhibit CD4$^{+}$ T cells within lung infiltrates. The absence of thymic VM expression in Aire$^{o/o}$ mice therefore allows the escape of VM-specific T cells that induce lung disease. A real-time PCR for VM was conducted on cDNA from purified thymic stroma of Aire$^{o/o}$ and Aire$^{+/+}$ mice and VM thymic expression was found to be Aire dependent, as was the expression of insulin, a known Aire-regulated antigen (FIG. 5C). As an additional control, GAD67 was tested and it was confirmed that this Aire-independent tissue specific protein was expressed equally in thymi from Aire$^{o/o}$ and Aire$^{+/+}$ mice (FIG. 5C) (13). To determine whether the number of IFN-γ-producing T cells with specificity for VM was increased in Aire$^{o/o}$ mice CD4+ T cells from Aire$^{o/o}$ and Aire$^{+/+}$ mice were assayed for VM specificity using an ELISPOT analysis (FIG. 5D). In this assay, Aire$^{o/o}$ mice showed a statistically significant increase in the number of IFN-γ producing, VM-specific T cells. These data demonstrate that an Aire-mediated defect in the development of tolerance in the thymus likely leads to the release of VM-specific T cells capable of inducing lung-specific tissue damage.

Figure 6A:
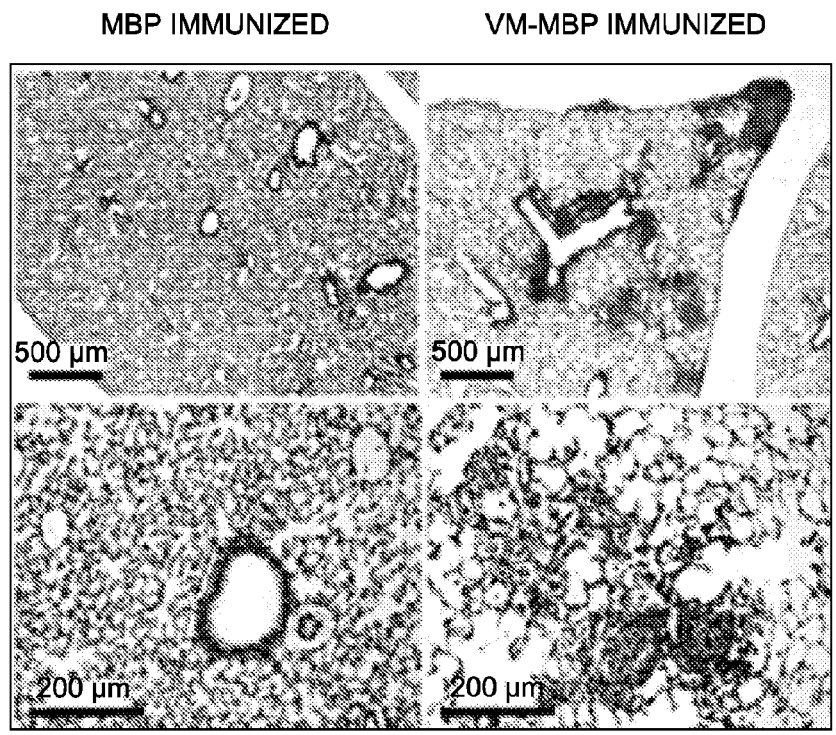
FIG. 6A shows H&E stains of lungs from BALB/c WT mice immunized with VM-MBP or MBP.
Figure 6B:
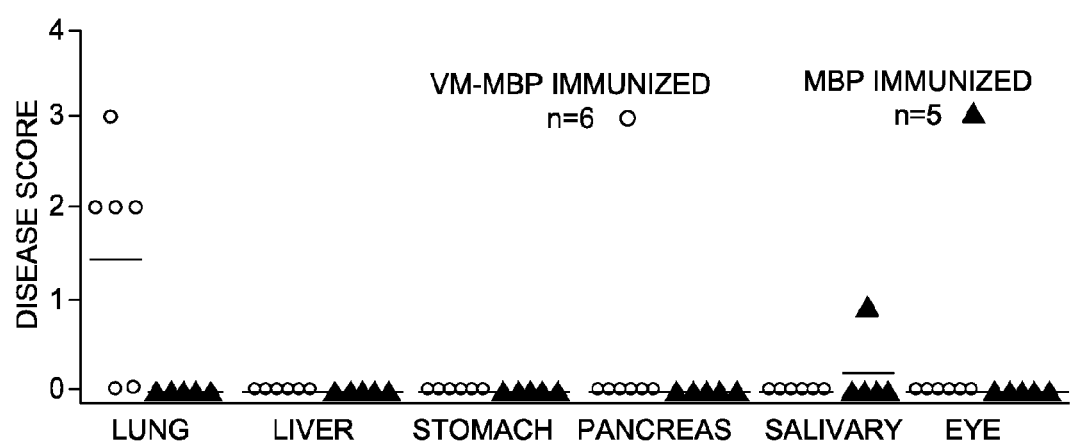
FIG. 6B shows that four of six mice immunized with VM-MBP exhibited lung disease, scored as shown. Mononuclear cell infiltrates were limited to the lung, except in one mouse immunized with MBP with salivary infiltrates. Lines indicate mean disease scores.
Figure 6C:
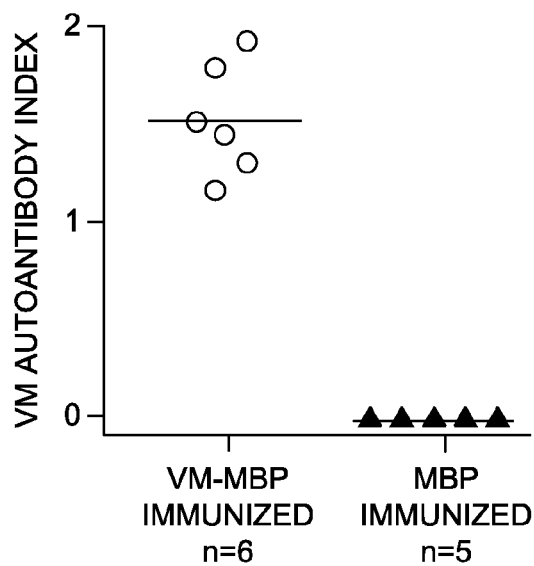
FIG. 6C represents results of a VM autoantibody assay, showing a VM-specific immune response in mice immunized with VM-MBP, but not in the MBP immunized controls.

Breaking tolerance to VM through adjuvant immunization. To determine if VM is a major lung autoantigen that by itself can induce pulmonary disease, an immunization protocol was devised in analogy to the experimental multiple sclerosis model Experimental Autoimmune Encephalomyelitis (EAE) (23). Using complete Freund's adjuvant (CFA) wild-type BALB/c mice we immunized with VM-MBP, followed by two additional rounds of immunization using VM-MBP in incomplete Freund's adjuvant (IFA). The mice were sacrificed and their organs analyzed for histology with H&E staining. The VM-MBP immunized mice developed lung disease similar to the spontaneous disease in Aire$^{o/o}$ mice and this disease was limited to the lung (FIG. 6A). A cohort of BALB/c wild-type mice immunized with the MBP protein tag with the same protocol did not develop lung disease (FIG. 6B). The sera from immunized mice were tested for VM antibodies and showed VM-specific immune reactivity in all of the VM immunized mice but not in the MBP-immunized controls (FIG. 6C). These results demonstrate that inducing a break in tolerance with adjuvant immunization can activate VM-specific cells to cause a lung-restricted disease similar to the spontaneous pulmonary infiltrates observed in Aire$^{o/o}$ mice.

Figure 7:
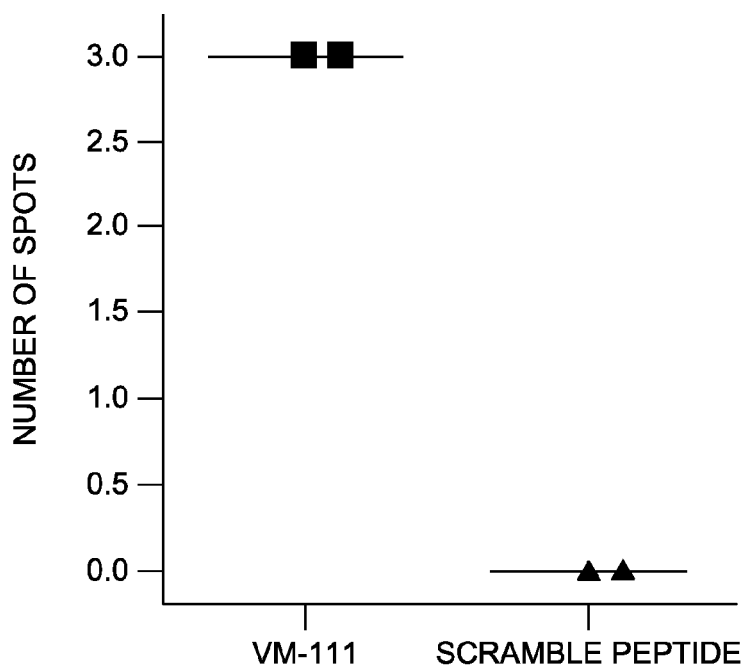
FIG. 7 shows the results of an ELISPOT analysis of T cells in Aire$^{0/0}$ mice. The ELISPOT analysis of IFN-γ-producing T cells in two BALB/c Aire$^{0/0}$ mice 12 weeks of age immunized with full length VM is presented. The Y axis indicates number of spots per 90,000 CD4$^+$ T cells.
Figure 8A:
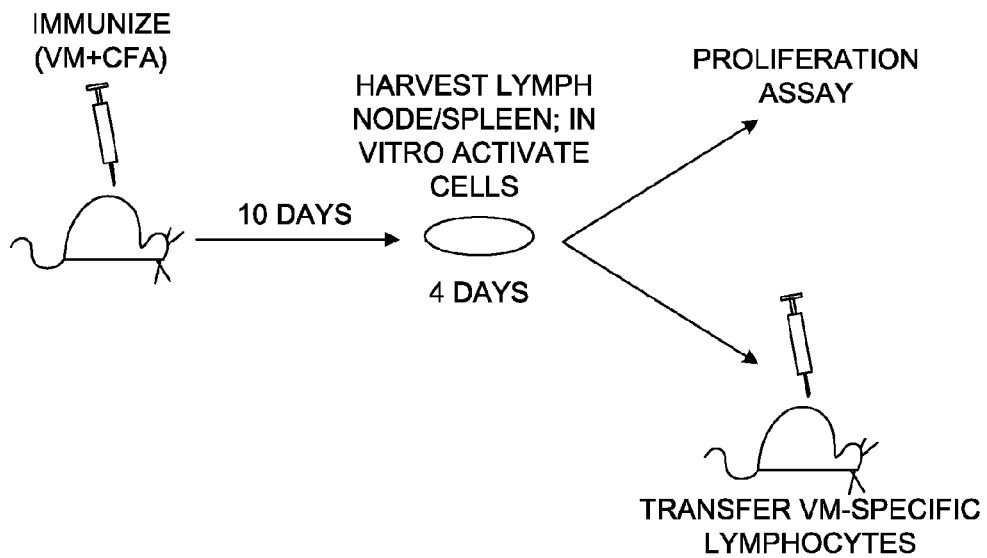
FIG. 8A introduces the protocol for adoptive transfer beginning with immunization of BALB/c WT mice with a VM or Ova peptide. Ten days later, lymph node and spleen cells were activated in vitro with respective peptides. Activated cells were analyzed in a proliferation assay or transferred into BALB/c SCID mice.
Figure 8B:
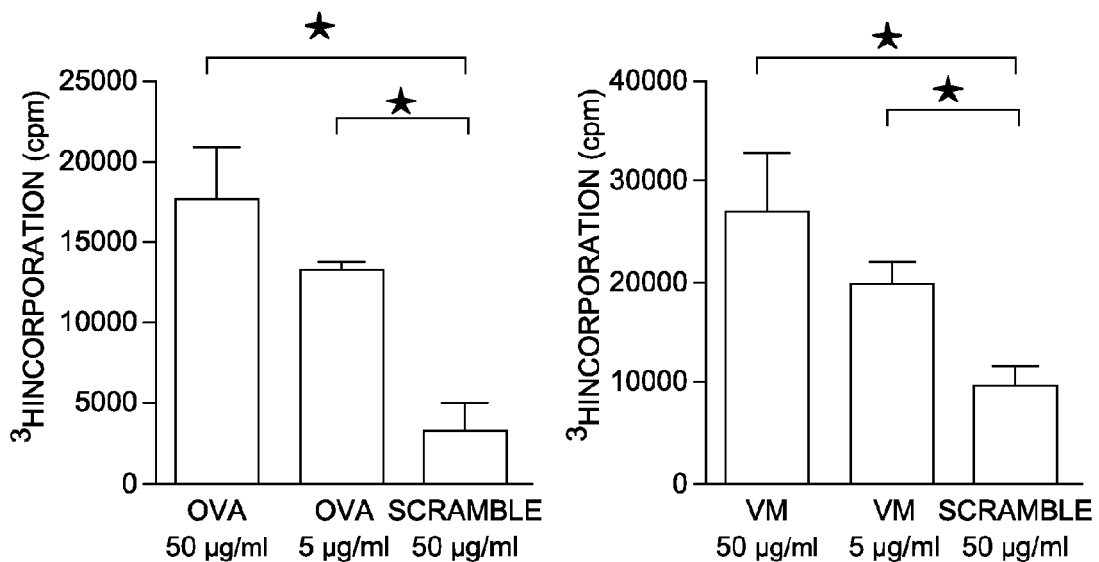
FIG. 8B shows results of representative [H$^3$] thymidine incorporation assays in cells harvested from immunized mice. Each condition was performed in triplicate; data are mean±SEM. The differences between Ova or VM peptides and scramble controls are statistically significant (*P<0.05 for all comparisons, two tailed t-test).
Figure 8C:
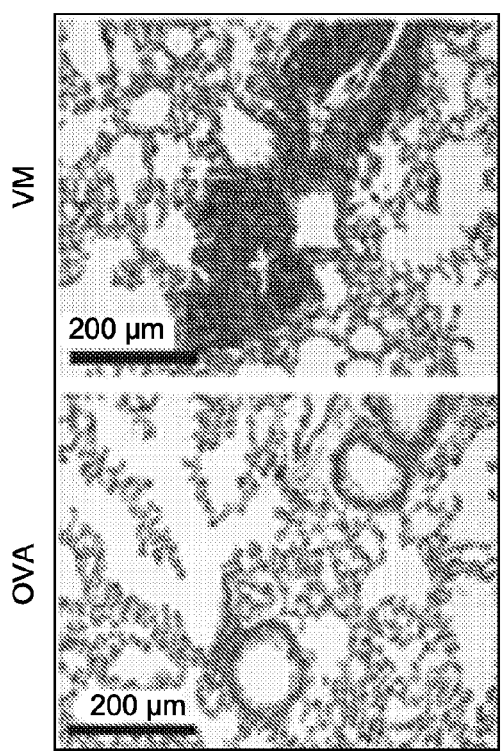
FIG. 8C displays H&E stains and histology analyses for organs harvested 4-6 weeks after VM specific lymphocytes were transferred into mice. The lung images revealed a mononuclear peribronchovascular infiltrate in the mouse receiving VM specific cells.
Figure 8D:
FIG. 8D displays disease scores of mice after adoptive transfer (AT) of antigen specific cells.

Lung specific disease from the adoptive transfer of activated VM-specific cells. One hallmark of autoimmune disease is that the adoptive transfer of activated antigen-specific cells to another host transfers the disease. Therefore a protocol was devised for the adoptive transfer of VM-specific immune cells harvested from immunized wild-type mice. To facilitate in vitro activation of the cells, VM peptides were generated that by computer modeling were predicted to bind to BALB/c MHC Class II, I-Ad (24). The peptides were then screened by ELISPOT analysis to determine whether Aire$^{o/o}$ mice had T cells specific for them. As shown in FIG. 7, Aire$^{o/o}$ mice had IFN-γ-producing T cells specific for the 15 amino acid peptide NLEGMLADVLNTVES (VM-111 set forth as SEQ ID NO: 8). The VM-111 peptide was used to immunize wild-type BALB/c mice and in vitro activate spleen and lymph node cells from these mice in conditions favoring the growth of CD4$^{+}$ T cells. A peptide derived from chicken ovalbumin (Ova) that is also known to bind I-A$^{d}$ was used as our negative control for the disease transfer (FIG. 8A). A portion of cells from immunized mice was analyzed by [H$^{3}$] thymidine incorporation to confirm that cells proliferated in response to our antigen (FIG. 8B). About 20×10$^{6}$ activated cells were adoptively transferred into each of our immunodeficient SCID mice, which were sacrificed 4 to 6 weeks later. The resulting lung disease was less severe than the spontaneous disease of Aire$^{o/o}$ mice, but the infiltrates were limited to the lung (FIGS. 8C-D) and had a similar appearance. These results show that the adoptive transfer of activated VM-specific cells can transfer lung disease and that the likely pathogenic effectors are CD4$^{+}$ T cells.

Figure 1B:
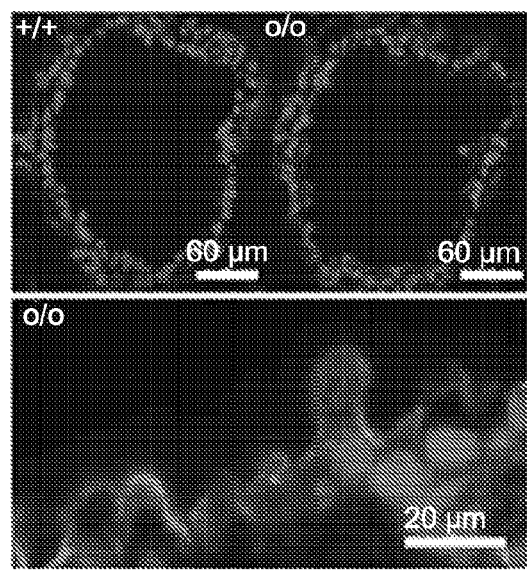
FIG. 1B depicts an indirect immunofluorescence stain with serum from a NOD Aire$^{o/o}$ mouse with pulmonary disease on frozen lung section from a immunodeficient SCID mouse. The lower panel depicts a higher magnification image of the lung section shown in upper right panel: Green, serum staining; blue, staining with nuclear marker 4',6'-diamidino-2-phenylindole (DAPI).
Figure 9B:
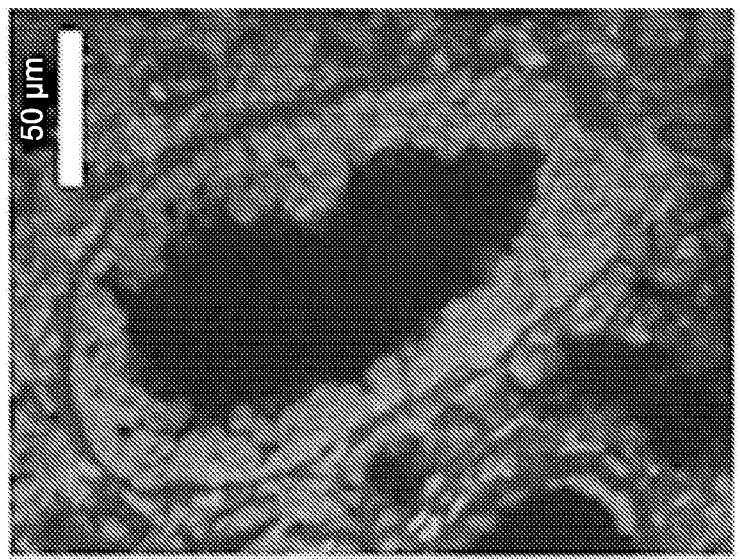
FIG. 9B shows results for a normal healthy patient. Green coloring represents serum staining, blue coloring represents staining with DAPI.
Figure 9A:
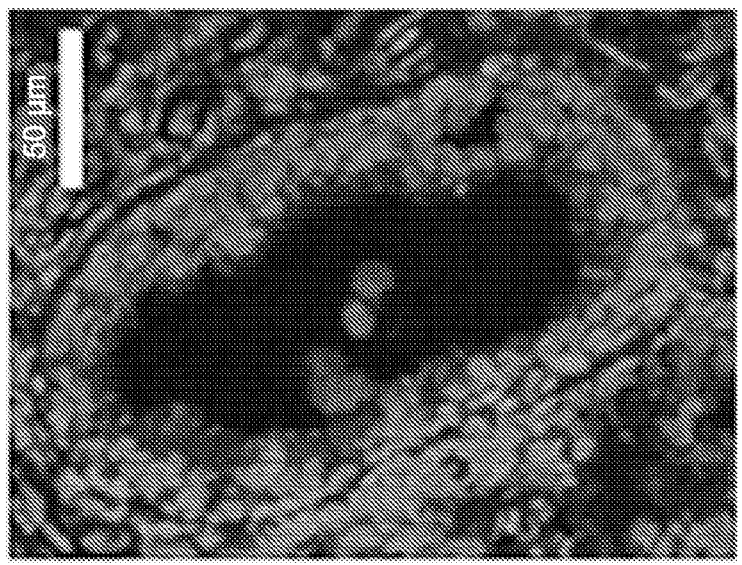
Figure 10:
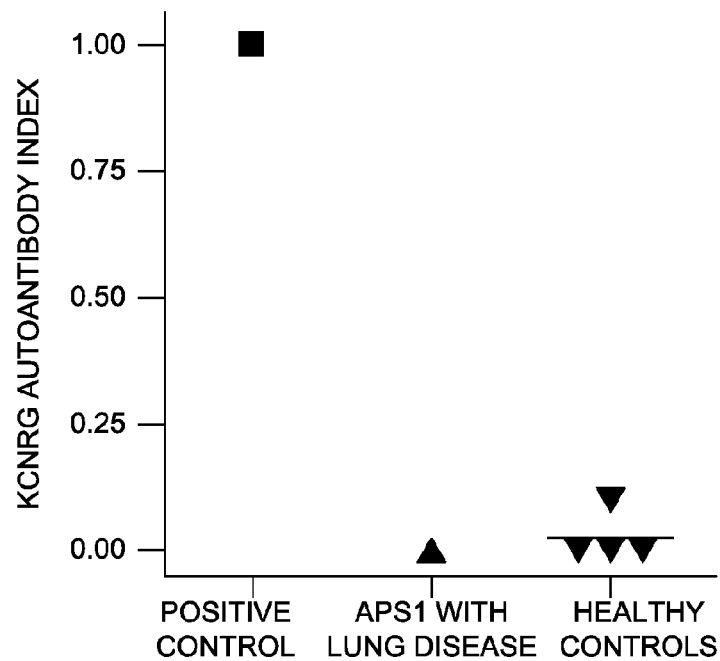
FIG. 10 shows the results of a KCNRG autoantibody assay in the APS1 patient with lung disease.

Autoreactivity to LPLUNC1, a VM-like protein, in a patient with APS1. Based on this data supporting an autoreactive lung response in Aire$^{o/o}$ mice, a similar response was investigated in an APS1 patient with lung disease. First, whether the patient exhibited an autoimmune response to lung tissue was tested by staining frozen sections of normal human lung with the patient's serum (FIG. 9A). The pattern of immunoreactivity was nearly identical to the pattern of staining seen using sera from Aire$^{o/o}$ mice (FIG. 1B, and FIG. 9A). The patient's serum did not contain autoantibodies to KCNRG, a bronchial epithelial antigen recently identified in APS1 (12) (FIG. 10).

Figure 9F:
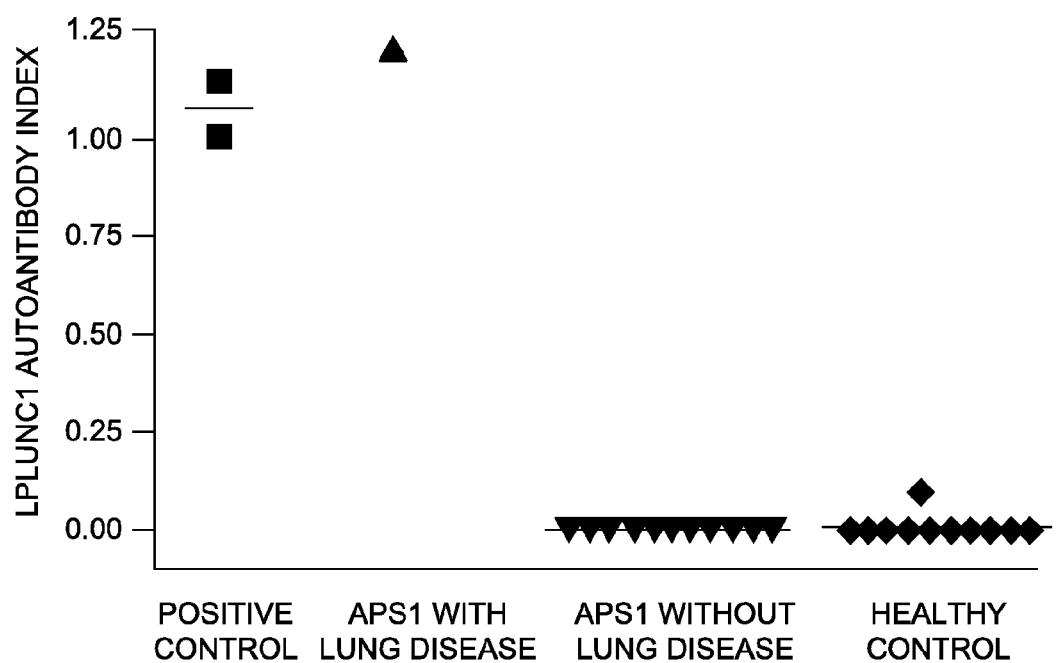
FIG. 9F shows results of an autoantibody assay, detecting autoantibodies to LPLUNC1 in serum from an APS1 patient with lung disease (n=1), healthy controls (n=11) and APS1 patients without lung disease (n=11). The assay was run in triplicate using in vitro transcribed and translated, radiolabeled human LPLUNC1 protein. As a positive control, two commercial anti-human LPLUNC1 antibodies were run. Representative results from 2 independent experiments are shown.
Figure 9G:
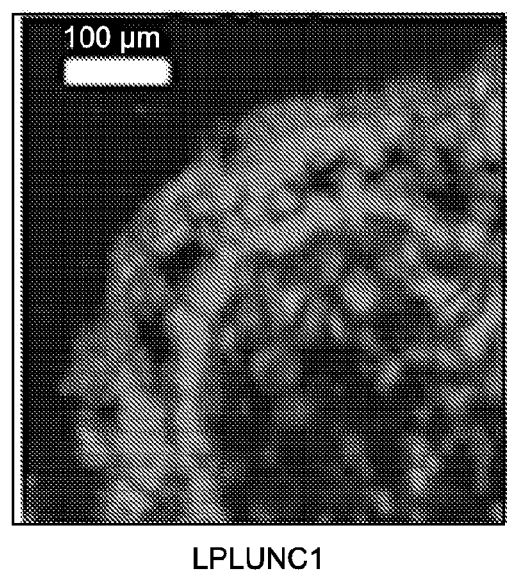
FIG. 9G shows normal frozen human lung stained by immunofluorescence with antibody to human LPLUNC1.
Figure 9H:
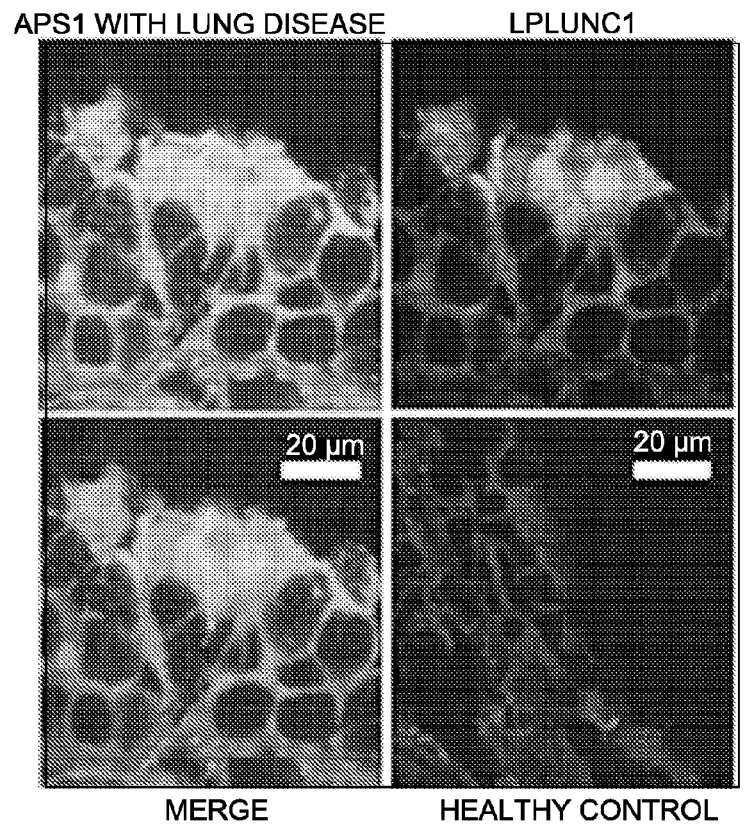
FIG. 9H depicts a high magnification view of a normal frozen human lung after immunofluorescence staining and shows the co-localization (bottom left) of serum from the APS1 patient with lung disease (top left, red) and the LPLUNC1 antibody (top right, green) on the bronchiolar epithelium. A serial lung section stained with healthy patient serum did not demonstrate autoreactivity.

A direct human homolog of mouse VM does not exist. On the basis of surveys of the University of California Santa Cruz and Ensembl genome databases, the human gene transcript orthologous to VM is C20orf115 and is likely an unprocessed pseudogene. The organization of the human genomic region containing C20orf115 is similar to that of the mouse, and it contains the PLUNC family of proteins, including LPLUNC1 (C20orf14), the adjacent transcript upstream from the human VM pseudogene (FIG. 9C). An analysis of the domain structure of VM using the NCBI Conserved Domain Database revealed that the VM protein shares the BPI (Bactericidal/Permeability Increasing protein) superfamily domain with the PLUNC (Palate, Lung, and Nasal epithelium Carcinoma associated protein) family of proteins located in the same region on mouse chromosome 2 (FIGS. 9D-E) (25). The PLUNC proteins have not previously been implicated in autoimmunity, but, because of their similar domain structure and expression pattern to VM, the APS1 patient serum was tested against LPLUNC1, the family member with the highest levels of gene expression in the lung, in particular the bronchiolar epithelium (26, 27). An autoantibody assay revealed that the APS1 patient with lung disease had immunoreactivity to LPLUNC1 that was not seen in the healthy controls or other samples from APS1 patients without lung disease (FIG. 9F) Immunofluorescent staining of normal human lung tissue with a human LPLUNC1 antibody showed that the protein is located on the bronchiolar epithelium in a pattern similar to the LPLUNC1 distribution in the APS1 patient (FIG. 9G-H). This data shows that the lung disease in an APS1 patient closely recapitulates the lung disease in Aire$^{o/o}$ mice, suggesting that LPLUNC1 is an important human lung autoantigen.

Figure 11:
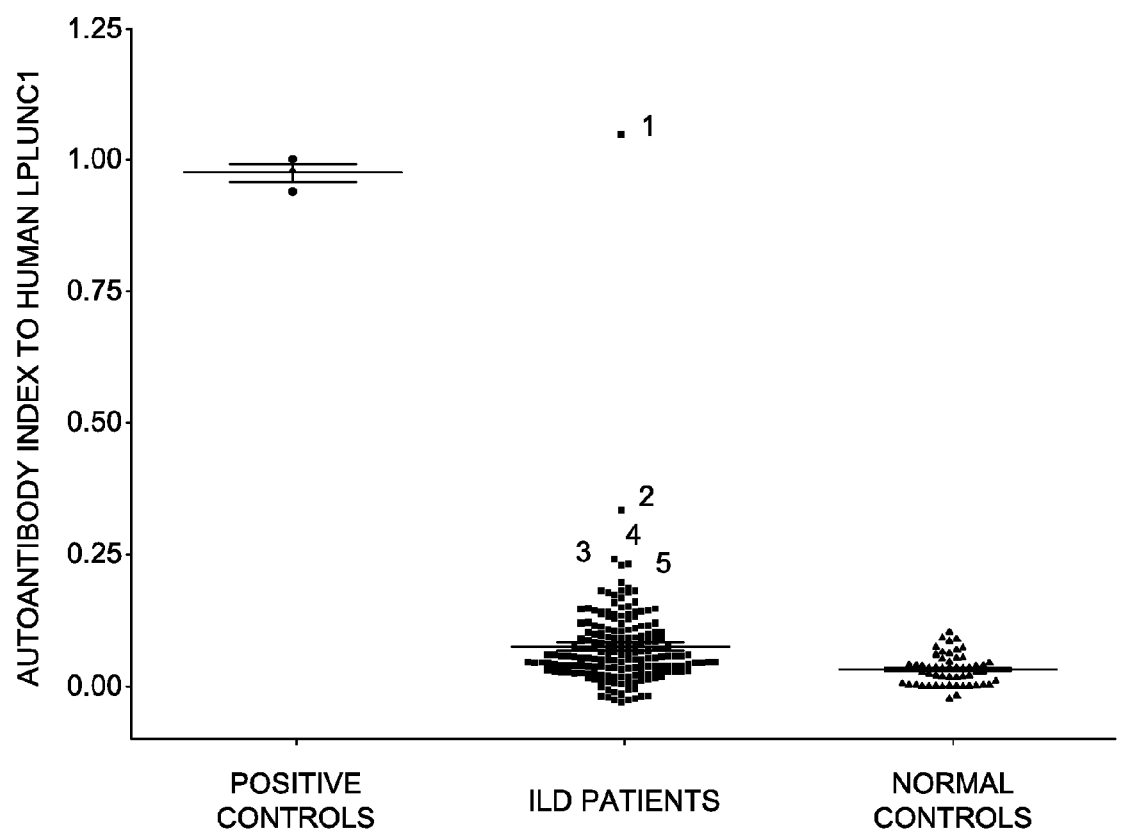
FIG. 11 provides a plot of the LPLUNC1 autoantibody index of three groups of subjects. Autoantibodies to human LPLUNC1 in serum from patients with ILD (n=186), normal control patients (n=54) and positive controls (n=3) were detected in an autoantibody assay run in triplicate using in vitro transcribed and translated, radiolabeled human LPLUNC1 protein.
Figure 12:
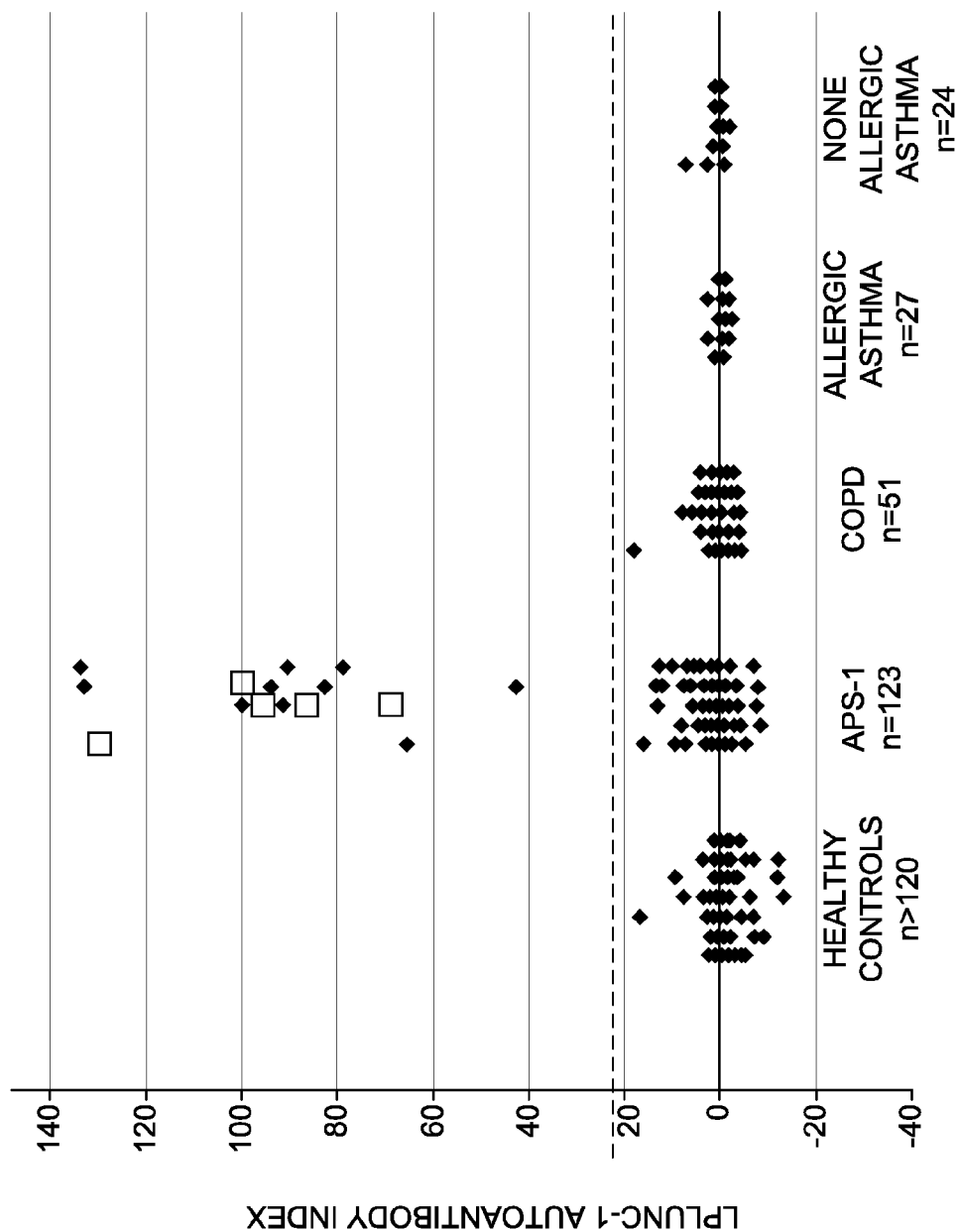
FIG. 12 provides the results of an autoantibody assay, detecting autoantibody to LPLUNC1 in serum from human subjects. The values shown in white boxes correspond to APS-1 patients with known interstitial lung disease. For comparison, patients with other known inflammatory lung disorders were also screened. None of the asthma or chronic obstructive pulmonary disease patients demonstrated autoreactivity to LPLUNC1. The assay was run using in vitro transcribed and translated, radiolabeled human LPLUNC1 protein.

As shown in FIG. 11, higher titers of autoantibodies to human LPLUNC1 (e.g., elevated LPLUNC1 autoantibody index) were detected in serum of ILD patients than in normal control subjects. In this assay, the positive controls included an APS1 patient with known LPLUNC1 autoantibody reactivity, and two commercial antibodies to human LPLUNC1. The ILD sera were obtained from a randomly selected subset of the patients seen and enrolled in the clinical database of the University of California, San Francisco (UCSF) ILD clinic. The normal controls are healthy subjects who do not have known autoimmunity or ILD.

TABLE 1

UCSF Interstitial Lung Disease (ILD) Patients by Diagnosis

| Diagnosis | Percentage (n = 548) |
|---|---|
| Idiopathic Pulmonary Fibrosis | 17% |
| Sarcoiditis | 12% |
| Hypersensitivity Pneumonitis | 12% |
| Scleroderma | 6% |
| Not ILD | 5% |
| Connective Tissue Disease - Undifferentiated | 5% |
| Non-specific Interstitial Pneumonia | 4% |
| Rheumatoid Arthritis | 4% |
| Myositis | 2% |
| Other Diagnoses | 14% |
| Unclassifiable | 9% |
| Not Reported | 7% |
| Pending Diagnosis | 4% |

TABLE 2

Baseline Characteristics of ILD Patients 1-5 of FIG. 11

| Patient | Age | Sex | LPLUNC1 Ab Index | Diagnosis | Evidence of Autoimmunity |
|---|---|---|---|---|---|
| 1 | 77 | F | 1.05 | Non-specific Interstitial Pneumonia (NSIP) | Rheumatoid Arthritis (CCP$^+$, RA$^+$) |
| 2 | 72 | M | 0.33 | Idiopathic Pulmonary Fibrosis | No |
| 3 | 46 | F | 0.24 | NSIP and Organizing Pneumonia | Dermatomyositis |
| 4 | 62 | F | 0.23 | Idiopathic NSIP and Bronchiolitis | No |
| 5 | 67 | M | 0.23 | Idiopathic Pulmonary Fibrosis | No |
| Negative Controls | — | — | 0.03 ± 0.03 | N/A | No |

TABLE 3

Figure 13:
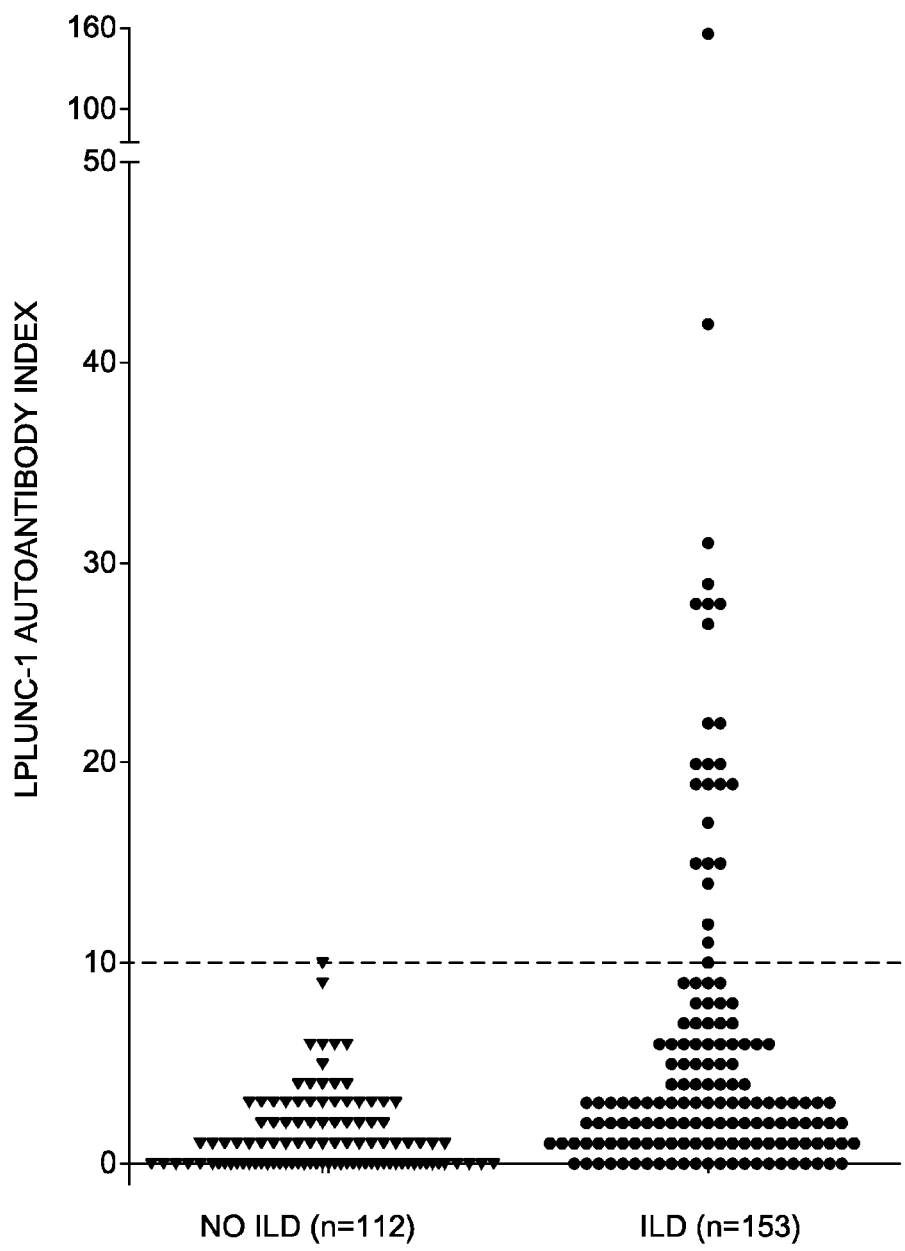
FIG. 13 provides results of an autoantibody assay, detecting autoantibody to LPLUNC1 in serum from human subjects with interstitial lung disease (n=153) and in normal controls (n=112). The autoantibody assay was run in duplicate using in vitro transcribed and translated, radiolabeled human LPLUNC1 protein. The interstitial lung disease (ILD) sera are from patients seen and enrolled in the clinical database of the UCSF ILD clinic. The normal controls were selected to age and race match the ILD patients as closely as possible, and are subjects who do not have known interstitial lung disease. The horizontal line depicts a value above which the specificity of the assay equals 100%, as determined by calculating the Receiver Operator Curve.

Baseline Characteristics of ILD Patients of FIG. 13

| Sex | Age (years) | Race | Diagnosis | LPLUNC AutoAb Index |
|---|---|---|---|---|
| Female | 76 | White | CTD-ILD | 156 |
| Male | 44 | Asian | CTD-ILD | 42 |
| Male | 57 | White | CTD-ILD | 31 |
| Male | 36 | White | Unclassifiable | 29 |
| Male | 45 | White | Idiopathic NSIP | 28 |
| Male | 71 | White | Idiopathic NSIP | 28 |
| Male | 77 | White | Unclassifiable | 28 |
| Male | 67 | White | CTD-ILD | 27 |
| Male | 68 | White | IPF | 22 |
| Female | 44 | Asian | Idiopathic NSIP | 22 |
| Male | 63 | White | CTD-ILD | 20 |
| Female | 70 | White | Idiopathic bronchiolitis | 20 |
| Male | 81 | White | IPF | 20 |
| Male | 59 | White | CTD-ILD | 19 |
| Female | 49 | Asian | CTD-ILD | 19 |
| Female | 58 | White | COP | 19 |
| Female | 82 | White | COP | 19 |
| Female | 70 | White | Unclassifiable | 17 |
| Female | 34 | White | CTD-ILD | 15 |
| Male | 63 | White | IPF | 15 |
| Female | 68 | White | Unclassifiable | 15 |
| Male | 74 | White | IPF | 14 |
| Male | 77 | White | Idiopathic bronchiolitis | 12 |
| Female | 46 | White | CTD-ILD | 11 |

* IPF, idiopathic pulmonary fibrosis; CTD-ILD, connective tissue disease associated-ILD; COP, cryptogenic organizing pneumonia; and NSIP, non-specific interstitial pneumonia.

FIG. 13 and Table 3 provide updates to FIG. 11 and Table 2, respectively.

Bovine lung tissue was stained using sera from an ILD patient with demonstrated positivity in the LPLUNC1 autoantibody assay. The staining showed that the patient serum reacts to the bronchiolar epithelium in a pattern similar to the LPLUNC1 distribution in the APS1 patient and in sections stained with a commercial LPLUNC1 antibody. For comparison, a control patient's sera was used to stain a serial section of tissue.

REFERENCES

1. Tansey et al., Variations in histological patterns of interstitial pneumonia between connective tissue disorders and their relationship to prognosis. Histopathology. 44, 585-596 (2004).

2. Jindal and Agarwal, Autoimmunity and interstitial lung disease. Curr. Opin. Pulm. Med. 11, 438-446 (2005).

3. Kinder et al., Idiopathic nonspecific interstitial pneumonia: lung manifestation of undifferentiated connective tissue disease? Am. J. Respir. Crit. Care Med. 176, 691-697 (2007).

4. Travis et al., Idiopathic nonspecific interstitial pneumonia: report of an American Thoracic Society project. Am. J. Respir. Crit. Care Med. 177, 1338-1347 (2008).

5. American Thoracic Society and European Respiratory Society, American Thoracic Society/European Respiratory Society International Multidisciplinary Consensus Classification of the Idiopathic Interstitial Pneumonias. Am. J. Respir. Crit. Care Med. 165, 277-304 (2002).

6. Ishii et al., Increased levels of interleukin-18 in bronchoalveolar lavage fluid of patients with idiopathic nonspecific interstitial pneumonia. Respiration. 72, 39-45 (2005).

7. Keogh and Limper, Characterization of lymphocyte populations in nonspecific interstitial pneumonia. Respir. Res. 6, 137 (2005).

8. Kakugawa et al., High serum concentrations of autoantibodies to HSP47 in nonspecific interstitial pneumonia compared with idiopathic pulmonary fibrosis. BMC Pulm. Med. 8, 23 (2008).

9. Yang et al., Detection of antivimentin antibody in sera of patients with idiopathic pulmonary fibrosis and non-specific interstitial pneumonia. Clin. Exp. Immunol. 128, 169-174 (2002).

10. Kurosu et al., Identification of annexin 1 as a novel autoantigen in acute exacerbation of idiopathic pulmonary fibrosis. J. Immunol. 181, 756-767 (2008).

11. Feghali-Bostwick et al., Cellular and humoral autoreactivity in idiopathic pulmonary fibrosis. J. Immunol. 179, 2592-2599 (2007).

12. Alimohammadi et al., Pulmonary autoimmunity as a feature of autoimmune polyendocrine syndrome type 1 and identification of KCNRG as a bronchial autoantigen. Proc. Natl. Acad. Sci. U.S.A. 106, 4396-4401 (2009).

13. Anderson et al., Projection of an immunological self shadow within the thymus by the aire protein. Science. 298, 1395-1401 (2002).

14. Cheng et al., What's new in the Aire? Trends Immunol. 28, 321-327 (2007).

15. Anderson et al., The cellular mechanism of Aire control of T cell tolerance. Immunity. 23, 227-239 (2005).

16. Liston et al., Aire regulates negative selection of organ-specific T cells. Nat. Immunol. 4, 350-354 (2003).

17. DeVoss et al., Spontaneous autoimmunity prevented by thymic expression of a single self-antigen. J. Exp. Med. 203, 2727-2735 (2006).

18. Hou et al., An aberrant prostate antigen-specific immune response causes prostatitis in mice and is associated with chronic prostatitis in humans. J. Clin. Invest. (2009).

19. Devoss et al., Effector mechanisms of the autoimmune syndrome in the murine model of autoimmune polyglandular syndrome type 1. J. Immunol. 181, 4072-4079 (2008).

20. Rangel-Moreno et al., Inducible bronchus-associated lymphoid tissue (iBALT) in patients with pulmonary complications of rheumatoid arthritis. J. Clin. Invest. 116, 3183-3194 (2006).

21. Khew-Goodall et al., Vomeromodulin, a putative pheromone transporter: cloning, characterization, and cellular localization of a novel glycoprotein of lateral nasal gland. FASEB J. 5, 2976-2982 (1991).

22. Walker and Abbas, The enemy within: keeping self-reactive T cells at bay in the periphery. Nat. Rev. Immunol. 2, 11-19 (2002).

23. Stromnes and Goverman, Active induction of experimental allergic encephalomyelitis. Nat. Protoc. 1, 1810-1819 (2006).

24. Bui et al., Automated generation and evaluation of specific MHC binding predictive tools: ARB matrix applications. Immunogenetics. 57, 304-314 (2005).

25. Marchler-Bauer et al., CDD: specific functional annotation with the Conserved Domain Database. Nucleic Acids Res. 37, D205-10 (2009).

26. Lonergan et al., Identification of novel lung genes in bronchial epithelium by serial analysis of gene expression. Am. J. Respir. Cell Mol. Biol. 35, 651-661 (2006).

27. Bingle and Craven, PLUNC: a novel family of candidate host defence proteins expressed in the upper airways and nasopharynx. Hum. Mol. Genet. 11, 937-943 (2002).

28. Marchal-Somme et al., Cutting edge: nonproliferating mature immune cells form a novel type of organized lymphoid structure in idiopathic pulmonary fibrosis. J. Immunol. 176, 5735-5739 (2006).

29. Mathis and Benoist, Aire. Annu. Rev. Immunol. 27, 287-312 (2009).

30. DeVoss, Shum and Anderson, unpublished data.

31. Bonasio et al., Clonal deletion of thymocytes by circulating dendritic cells homing to the thymus. Nat. Immunol. 7, 1092-1100 (2006).

32. Vafiadis et al., Insulin expression in human thymus is modulated by INS VNTR alleles at the IDDM2 locus. Nat. Genet. 15, 289-292 (1997).

33. Giraud et al., An IRF8-binding promoter variant and AIRE control CHRNA1 promiscuous expression in thymus. Nature. 448, 934-937 (2007).

34. Canny and Levy, Bactericidal/permeability-increasing protein (BPI) and BPI homologs at mucosal sites. Trends Immunol. 29, 541-547 (2008).

35. Barnes et al., Pulmonary Genomics, Proteomics, and PLUNCs. Am. J. Respir. Cell Mol. Biol. 38, 377-379 (2008).

36. Langrish et al., IL-23 drives a pathogenic T cell population that induces autoimmune inflammation. J. Exp. Med. 201, 233-240 (2005).

We claim:

1. A method for assessing whether a mammalian patient has or is predisposed to an interstitial lung disease (ILD), said method comprising:

a) performing an antibody-based assay to quantitate lung autoantigen-reactive autoantibodies in a biological sample from the patient, wherein the lung autoantigen is a long palate, lung, and nasal epithelium carcinoma-associated protein 1 (LPLUNC1) or a LPLUNC1-like protein comprising the amino acid sequence at least 70% identical to SEQ ID NO:2; and b) detecting an elevated level of the lung autoantigen-reactive autoantibodies in said biological sample as compared to a control biological sample thereby determining the patient has ILD or a predisposition to ILD.

2. The method of claim 1, wherein the lung autoantigen is a long palate, lung, and nasal epithelium carcinoma-associated protein 1 (LPLUNC 1).

3. The method of claim 1, wherein the lung autoantigen is a LPLUNC1-like protein comprising the amino acid sequence at least 70% identical to SEQ ID NO:2.

4. The method of claim 1, wherein the biological sample is selected from a group consisting of blood, plasma, serum, bronchial alveolar lavage (BAL) fluid, and lung tissue.

5. The method of claim 1, wherein the patient has or is suspected of having a systemic autoimmune disease.

6. The method of claim 5, wherein the systemic autoimmune disease is selected from the group consisting of rheumatoid arthritis, scleroderma, Sjogren's syndrome, systemic lupus erythematosis, sarcoidosis, Wegener's granulomatosis, and autoimmune polyendocrine syndrome type 1 (APS-1).

7. The method of claim 1, wherein the antibody-based assay is selected from the group consisting of ELISA, Western blotting, immunofluorescence analysis, flow cytometry, and antibody microarray.

8. The method of claim 7, wherein said antibody-based assay comprises a first reagent that specifically binds to said lung autoantigen-reactive autoantibodies, and a second reagent for detecting said autoantibodies, wherein said first reagent is the lung autoantigen or a cell expressing the lung autoantigen, and said second reagent comprises a secondary antibody that is reactive with constant regions of the autoantibodies.

9. The method of claim 1, further comprising performing one or both of a pulmonary function test and a high resolution computed tomography scan on said patient.

10. The method of claim 1, further comprising: c) administering a treatment to the patient when the elevated level of the lung autoantigen-reactive autoantibodies is detected.

11. The method of claim 10, wherein said treatment is selected from the group consisting of a corticosteroid, cyclophosphamide, mycophenolate mofetil, and azathioprine.

12. The method of claim 10, wherein said treatment comprises a mucosal tolerance regimen comprising dispensing a formulation to the patient by an oral or an intra-nasal route, wherein the formulation comprises a pharmaceutically acceptable excipient, and an effective amount of the lung autoantigen, or a peptide derived therefrom.

13. The method of claim 10, wherein said treatment comprises a parenteral tolerance regimen comprising dispensing a formulation to the patient by intravenous or subcutaneous injection, wherein the formulation comprises an effective amount of the lung autoantigen, a peptide derived therefrom, or a nucleic acid encoding the lung autoantigen in operable combination with a regulatory sequence.

14. The method of claim 10, wherein said treatment comprises an antigen-coupled cell tolerance regimen comprising dispensing a formulation to the patient by intravenous injection, wherein the formulation comprises an effective amount of the lung autoantigen, or a peptide derived therefrom, wherein the autoantigen or the peptide is coupled to ethylene carbodiimide-fixed, autologous antigen presenting cells.

15. The method of claim 10, wherein said treatment comprises a regulatory T cell regimen comprising dispensing a formulation to the patient by intravenous injection, wherein the formulation comprises an effective amount of ex vivo-expanded lung autoantigen-specific regulatory T cells.

* * * * *